United States Patent
Quinonez

(10) Patent No.: US 9,365,418 B2
(45) Date of Patent: Jun. 14, 2016

(54) UNIVERSAL HARDWARE PLATFORM AND TOOLSET FOR OPERATING AND FABRICATING MICROFLUIDIC DEVICES

(75) Inventor: Carlo Joseph Quinonez, San Deigo, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 2 days.

(21) Appl. No.: 14/241,975

(22) PCT Filed: Sep. 4, 2012

(86) PCT No.: PCT/US2012/053703
§ 371 (c)(1),
(2), (4) Date: Feb. 28, 2014

(87) PCT Pub. No.: WO2013/033726
PCT Pub. Date: Mar. 7, 2013

(65) Prior Publication Data
US 2014/0220173 A1    Aug. 7, 2014

Related U.S. Application Data

(60) Provisional application No. 61/530,623, filed on Sep. 2, 2011, provisional application No. 61/594,938, filed on Feb. 3, 2012.

(51) Int. Cl.
*B81C 99/00* (2010.01)
*B29C 45/17* (2006.01)
(Continued)

(52) U.S. Cl.
CPC .............. *B81C 99/0085* (2013.01); *B01L 1/025* (2013.01); *B01L 3/502707* (2013.01); *B01L 3/502715* (2013.01); *B29C 45/1753* (2013.01); *B29C 45/34* (2013.01); *B29C 45/401* (2013.01); *F04B 19/006* (2013.01); *F04B 43/043* (2013.01); *F04B 49/065* (2013.01);
(Continued)

(58) Field of Classification Search
CPC ..................... G01N 2035/00158; B01L 1/025; B01L 3/502707; B01L 3/502715; B01L 2200/027; B01L 2200/028; B01L 2300/0645; B01L 2400/0481; B01L 2400/0487; F04B 43/043; F04B 49/065; F04B 19/006; B29C 45/34; B29C 45/1753; B29C 45/401; B29C 2045/0094; Y10T 137/8376; G05D 7/0694; B81C 99/0085; B81C 2201/034
USPC ........................................................ 700/266
See application file for complete search history.

(56) References Cited

U.S. PATENT DOCUMENTS 3,647,337 A    3/1972  Dega
5,295,658 A    3/1994  Atkinson et al.
(Continued)

OTHER PUBLICATIONS

International Preliminary Report on Patentability issued Mar. 4, 2014 and Written Opinion mailed Nov. 16, 2012 in connection with corresponding International Application No. PCT/US2012/053703 (8 pages total).
(Continued)

*Primary Examiner* — Shogo Sasaki
(74) *Attorney, Agent, or Firm* — Mark D. Wieczorek; Mayer & Williams PC

(57) ABSTRACT

A microfluidic device platform may include a valve manifold adapted to deliver a programmable pressure to a plurality of ports, a cell chamber having programmable environmental control, and a chip-to-world interface.

18 Claims, 27 Drawing Sheets

(51) Int. Cl.
    *F04B 19/00*       (2006.01)
    *F04B 43/04*       (2006.01)
    *F04B 49/06*       (2006.01)
    *G05D 7/06*        (2006.01)
    *B01L 1/02*        (2006.01)
    *B01L 3/00*        (2006.01)
    *B29C 45/34*       (2006.01)
    *B29C 45/40*       (2006.01)
    *G01N 35/00*       (2006.01)
    *B29C 45/00*       (2006.01)

(52) U.S. Cl.
    CPC ........ *G05D 7/0694* (2013.01); *B01L 2200/027* (2013.01); *B01L 2200/028* (2013.01); *B01L 2300/0645* (2013.01); *B01L 2400/0481* (2013.01); *B01L 2400/0487* (2013.01); *B29C 2045/0094* (2013.01); *B81C 2201/034* (2013.01); *G01N 2035/00158* (2013.01); *Y10T 137/8376* (2015.04)

(56) References Cited

U.S. PATENT DOCUMENTS

| | | | | |
|---|---|---|---|---|
| 5,424,209 | A * | 6/1995 | Kearney | C12M 41/48 435/286.5 |
| 5,863,502 | A * | 1/1999 | Southgate | B01J 19/0046 422/417 |
| 6,416,718 | B1 * | 7/2002 | Maiefski | B01J 19/0046 222/144.5 |
| 6,805,841 | B2 * | 10/2004 | Shvets | A61M 5/1452 422/50 |
| 2002/0063060 | A1 * | 5/2002 | Gascoyne | B01L 3/5027 204/471 |
| 2002/0110905 | A1 * | 8/2002 | Barbera-Guillem | C12M 23/24 435/294.1 |
| 2002/0192112 | A1 * | 12/2002 | Chow | B01L 3/502715 422/63 |
| 2004/0223874 | A1 * | 11/2004 | Numajiri | B01L 3/502715 422/400 |
| 2004/0224339 | A1 * | 11/2004 | Numajiri | B01L 3/502715 435/6.18 |
| 2005/0209629 | A1 | 9/2005 | Kerr et al. | |
| 2005/0214173 | A1 * | 9/2005 | Facer | B01L 3/502707 422/400 |
| 2005/0223813 | A1 * | 10/2005 | Lull | G01F 1/696 73/861 |
| 2005/0288825 | A1 | 12/2005 | Tinsley et al. | |
| 2007/0166199 | A1 | 7/2007 | Zhou et al. | |
| 2009/0178934 | A1 | 7/2009 | Jarvius et al. | |
| 2010/0190265 | A1 | 7/2010 | Dufva et al. | |
| 2011/0006463 | A1 | 1/2011 | Layman | |
| 2011/0020856 | A1 | 1/2011 | Poo et al. | |

OTHER PUBLICATIONS

International Search Report for PCT/US12/53703 dated Oct. 12, 2012.

* cited by examiner

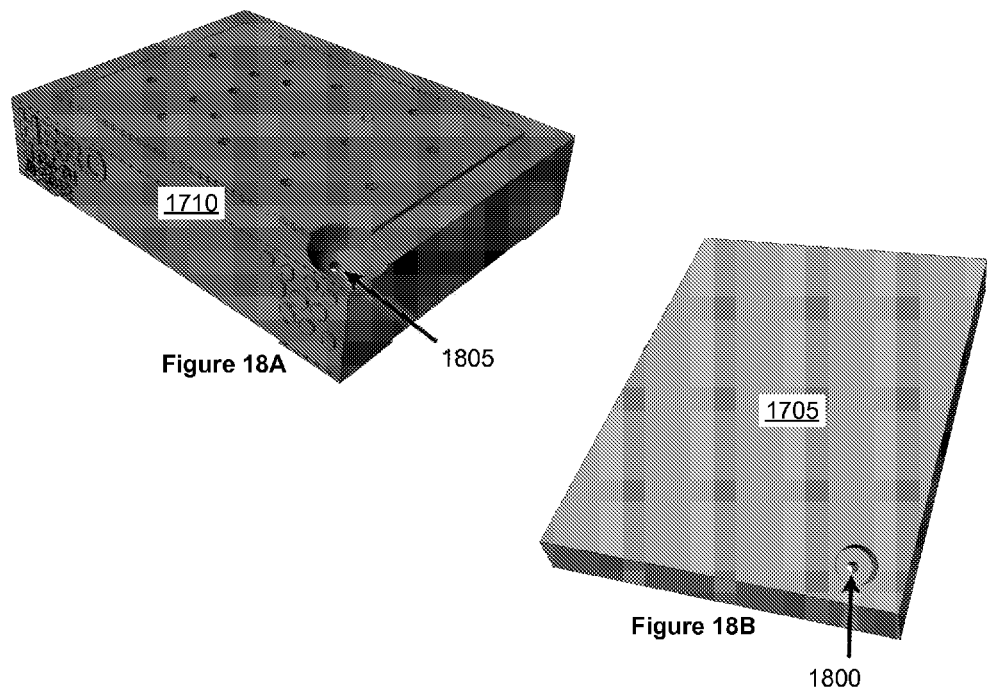
Figure 18A
Figure 18B
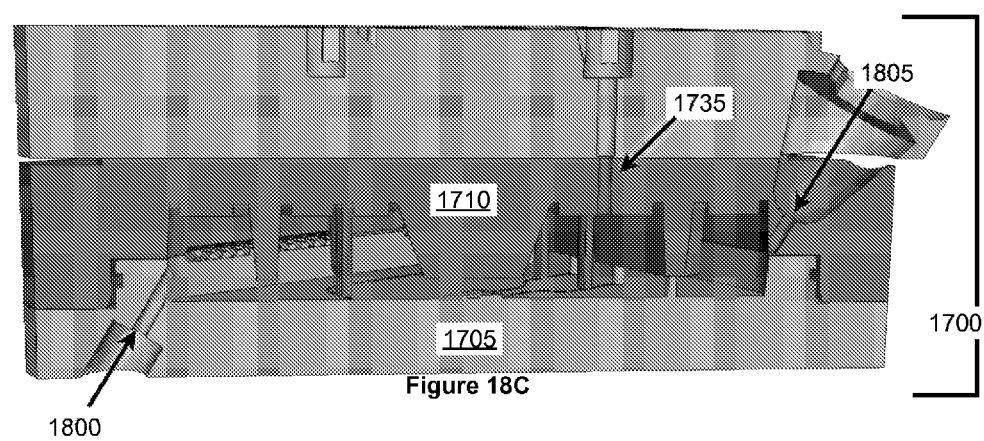
Figure 18C

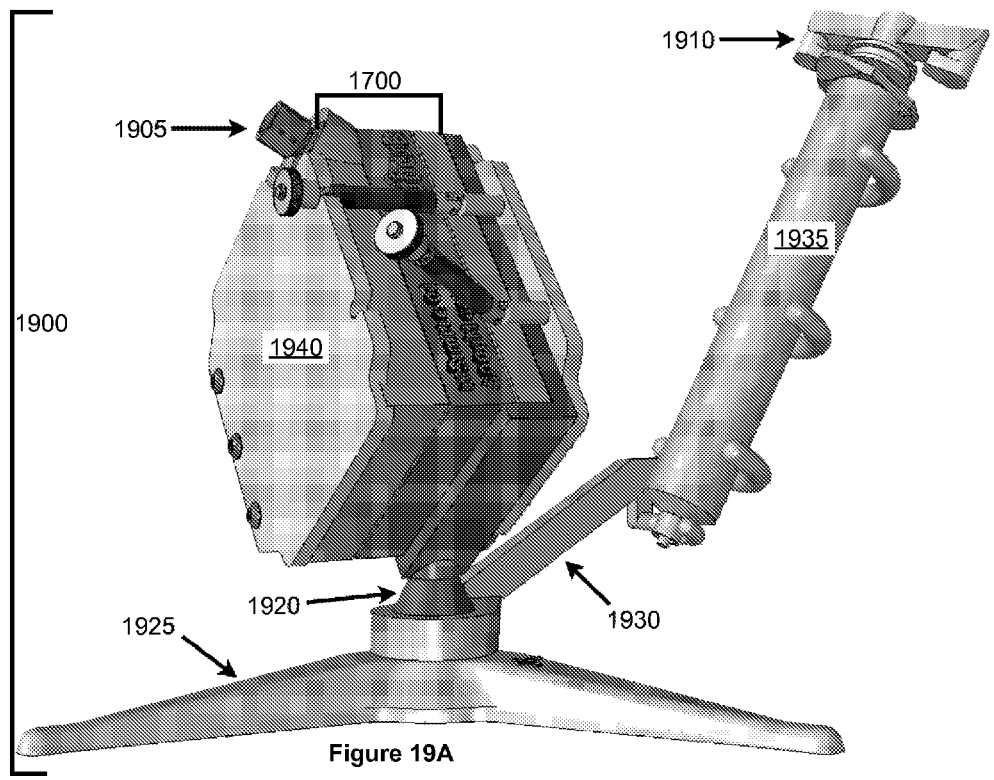
Figure 19A
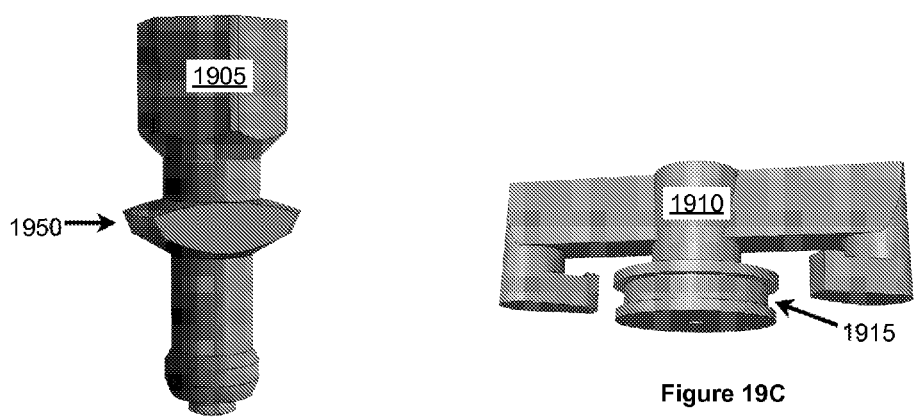
Figure 19B
Figure 19C

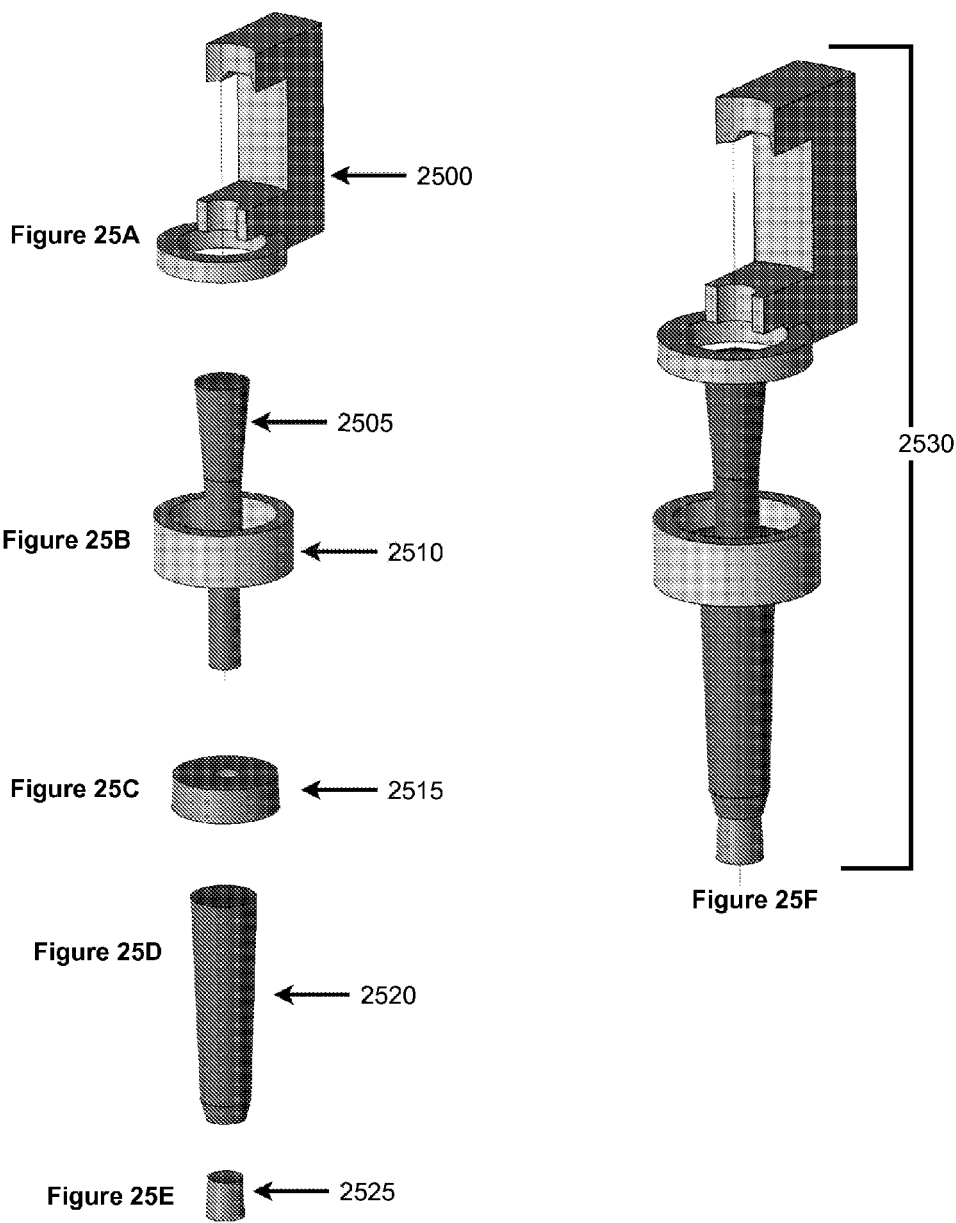
Figure 25A — 2500
Figure 25B — 2505, 2510
Figure 25C — 2515
Figure 25D — 2520
Figure 25E — 2525
Figure 25F — 2530

UNIVERSAL HARDWARE PLATFORM AND TOOLSET FOR OPERATING AND FABRICATING MICROFLUIDIC DEVICES

CROSS REFERENCE TO RELATED APPLICATIONS

This application claims the priority benefit of provisional application No. 61/530,623, filed Sep. 2, 2011, and provisional No. 61/594,938 filed Feb. 3, 2012.

STATEMENT REGARDING FEDERALLY SPONSORED RESEARCH AND DEVELOPMENT

This invention was made with Government support under Grant Nos. GM06852 and GM085764 awarded by the NIH. The Government has certain rights in this invention.

BACKGROUND OF THE INVENTION

The present invention generally relates to apparatus and methods for fabricating active microfluidic features such as valves and pumps.

The automation and greater reproducibility of microfluidic techniques make them ideally suited to collecting the amount of single-cell data required in Systems Biology research. Advances in microscopy have made single cell analysis an important approach in both the study of cell signaling pathways and in content analysis used in drug development. Microfluidic techniques have further enhanced these approaches and there has been an enormous explosion of new assays and techniques developed to exploit the advantages of this approach. One of the bottlenecks in the growth of microfluidics has been the lack of availability and the expense of devices to implement these experiments.

Existing methods for fabrication of active microfluidic features require two layers. Typically, existing methods use "flow" and "control" layers that are independently fabricated, aligned and bonded.

As can be seen, there is a need for apparatus and methods for improving the availability of microfluidic features.

TERMINOLOGY

"Pneumatic circuit" herein refers to a plurality of tortuous gas-tight passageways, within a monolithic body, connecting a plurality of inputs and outputs. By analogy, a pneumatic circuit is to gases as a printed circuit board is to electricity.

"Elastomeric matrix" herein refers to a casting produced using a polymerized elastomer, such as silicone rubber.

Compound words incorporating "chip" (e.g. chip-to-world interface, on-chip reservoirs) herein refers to an elastomeric matrix configured with microfluidic features such as valves, channels, and reservoirs.

SUMMARY OF THE INVENTION

In one aspect of the invention, a modular control system for operating a pressure-driven microfluidic device, comprises a base including both electrical and pneumatic connections; one or more pneumatic control modules including a plurality of pneumatic output ports; and an electrical bus and a pneumatic bus common to the base module and the one or more pneumatic control modules.

In another aspect of the invention, an apparatus for casting elastomeric devices comprises a sealed mold with an inlet and vent; a stand configured to orient the sealed mold so the inlet is at a low-point of a mold cavity and the vent is at a high-point of the mold cavity; a means for securing the mold when pressurized; a syringe barrel connected to the sealed mold, with a volume larger than the internal cavity of the mold; and a means configured to apply pneumatic pressure to the syringe barrel.

In another aspect of the invention, an elastomeric matrix comprises a plurality of channels for flowing liquid, a plurality of features interlocking with a chip-to-world interface; a plurality of on-chip reservoirs; and a plurality of vias connecting the on-chip reservoirs to the plurality of channels.

These and other features, aspects and advantages of the present invention will become better understood with reference to the following drawings, description and claims.

BRIEF DESCRIPTION OF THE DRAWINGS

FIG. 18A illustrates a perspective view of venting features on the upper mold component;

FIG. 18B illustrates a perspective view of injection features on the lower mold component;

FIG. 18C illustrates a perspective section view of an assembled double-sided mold;

FIG. 19A illustrates a perspective view of a casting apparatus;

FIG. 19B illustrates a perspective view of a vent fitting comprising the casting apparatus;

FIG. 19C illustrates a perspective view of a pneumatic syringe adaptor comprising the casting apparatus;

FIG. 25A illustrates a perspective view of isolated upper interface base feature comprising crimp-capture retention;

FIG. 25B illustrates a perspective view of isolated lower interface base features comprising on-interface walls and pneumatic passageway;

FIG. 25C illustrates a perspective view of isolated upper mold knockout base feature comprising on-chip solution reservoir;

FIG. 25D illustrates a perspective view of isolated upper mold buildup base feature comprising on-chip solution reservoir;

FIG. 25E illustrates a perspective view of isolated lower mold buildup base feature comprising on-chip solution reservoir;

FIG. 25F illustrates a perspective view of design features comprising on-chip reservoir configured with reservoir-access port;

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, embodiments of the present invention generally provide a single-layer approach to active microfluidic features that may lower tooling costs, improve manufacturing yields and improve compatibility with traditional injection-molding processes, as compared to conventional microfluidic features. Tooling costs may be reduced because only a single mold is required. Manufacturing yields may be improved because the difficult secondary operations of alignment and bonding may be eliminated. Together, these improvements may enable the creation of microfluidic devices with active features to be produced using conventional liquid injection molding techniques and only a single secondary operation (substrate bonding).

Figure 1A:
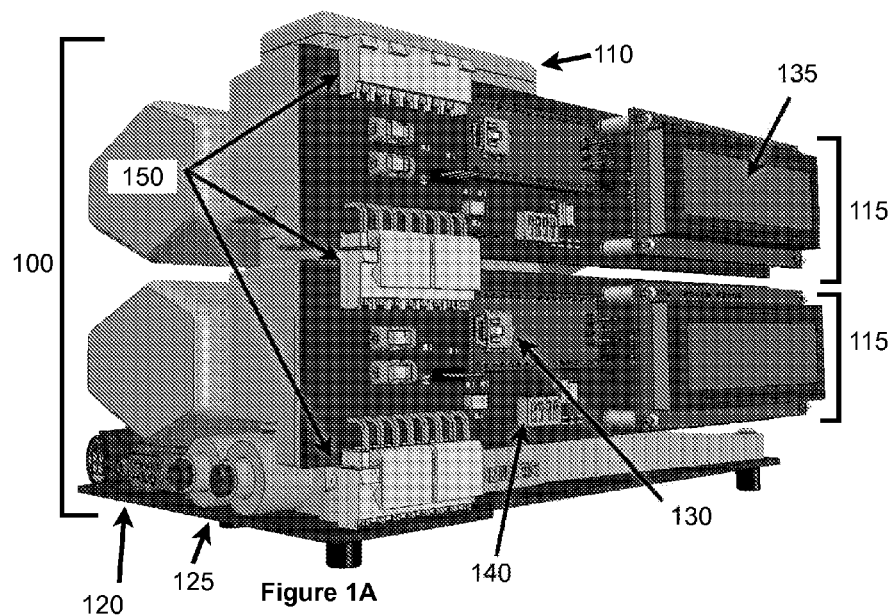
FIG. 1A illustrates a perspective view of a control stack, configured with a base module and a two pneumatic output modules, for operating microfluidic devices.

With reference to FIG. 1A, a control stack (100) is configured with a base (105), cap (110) and two identical pneumatic output (herein abbreviated PO) modules (115). The base (105) provides a single set of electrical (120) and pneumatic (125) connections, which are shared among the modules comprising the control stack. The PO-module printed circuit assembly (herein abbreviated PCA) (155) is comprised of: a microcontroller (130) which may be reprogrammed in the field; an LCD (135) providing information on the current operation of the module; and DIP switches (140) allowing user to directly configure microcontroller operations. Although a plurality of suitable microcontrollers exist, an open-source microcontroller platform, such as Arduino, facilitates development by non-traditional hardware developers.

Figure 1B:
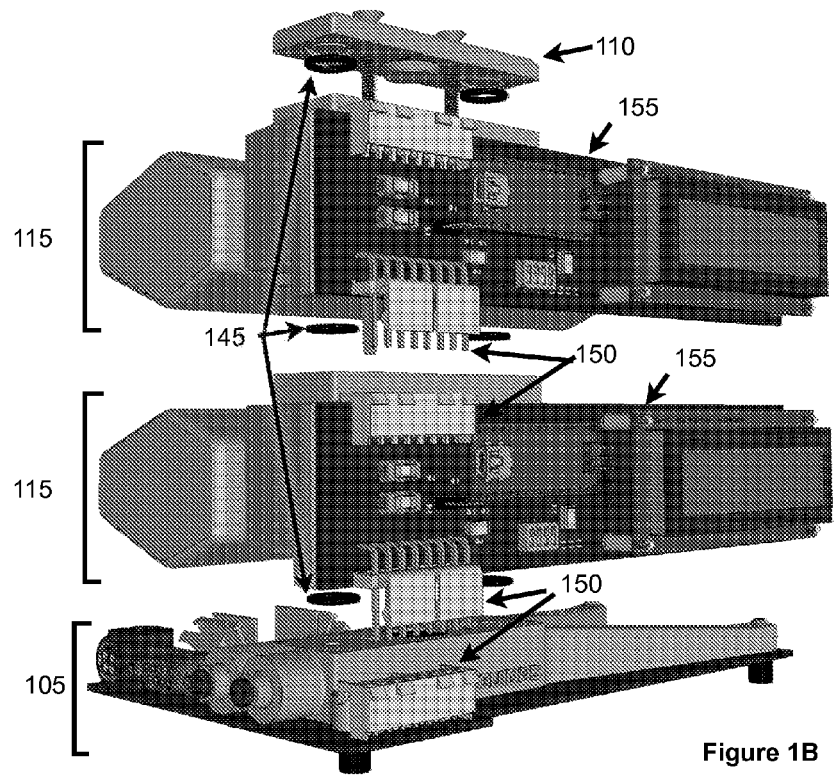
FIG. 1B illustrates a perspective exploded view of the control stack illustrated in FIG. 1A.

With reference to FIG. 1B, the control stack of FIG. 1A is exploded to reveal backplane details. O-rings (145) in a standard static face-seal configuration improve performance of pneumatic backplane. Electrical connectors (150) carry power supply and a digital network. The intra-stack digital network is used to coordinate the operation of the hardware. Hardware performance data may be monitored and transmitted over the intra-stack digital network to a monitoring system. The monitoring system may analyze the performance data for predictors of operational failure.

Figure 2:
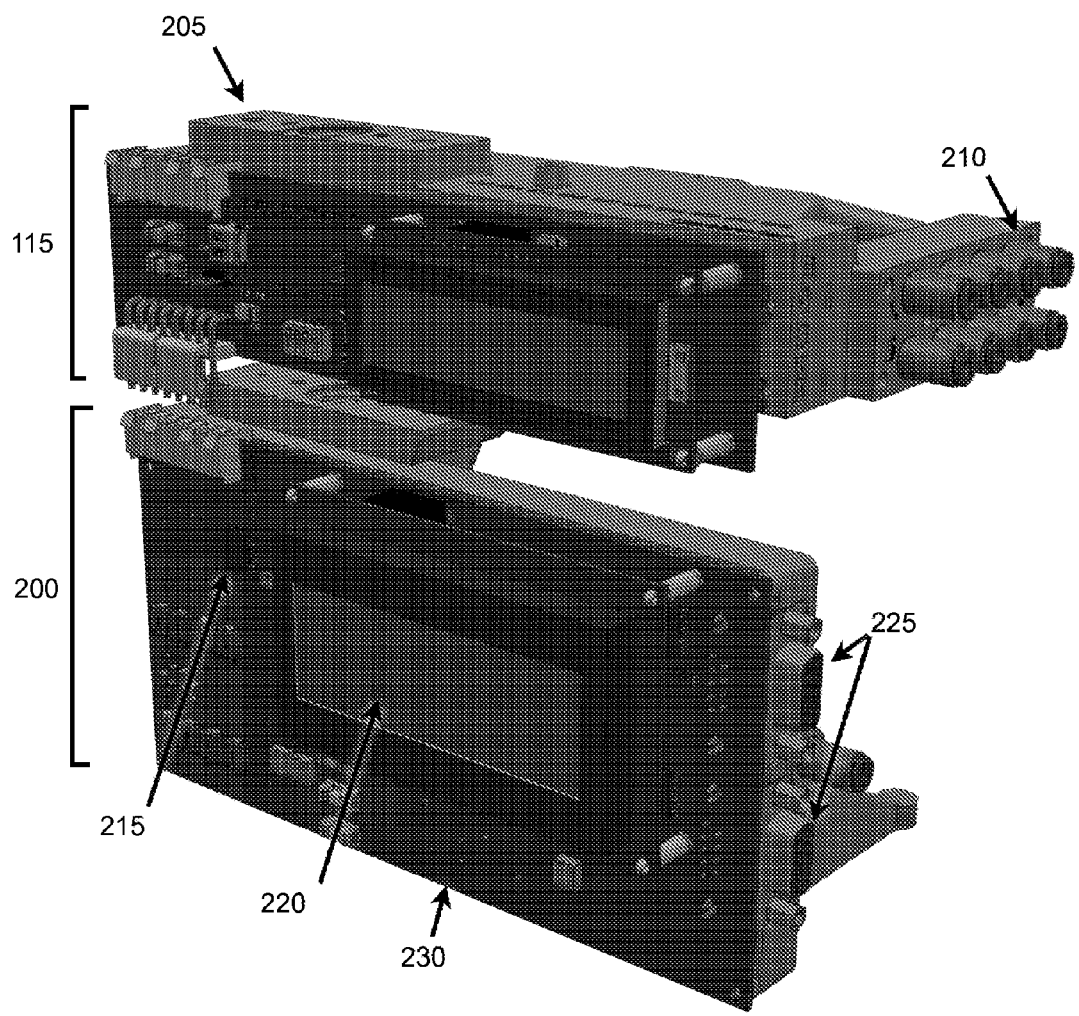
FIG. 2 illustrates a perspective view of an environmental chamber controller configured as a base module in a control stack configured with one pneumatic output module.

With reference to FIG. 2, a control stack is comprised of a PO module 115 and Environmental Chamber Controller module (herein abbreviated ECC) (200). The illustrated stack lacks a base and pneumatic backplane is uncapped (205). As illustrated, the PO module provides eight output channels (210) configured with, for example, ⅛"-OD Push-To-Connect fittings (herein abbreviated PTC). The ECC module printed circuit assembly (230) is comprised of: a microcontroller (215) which may be reprogrammed in the field; an LCD (220) providing information on the current operation of the module. Although a plurality of suitable microcontrollers exist, an open-source microcontroller platform, such as Arduino, facilitates development by non-traditional hardware developers. Each control connector (225) accommodates peripherals such as the environmental chamber of FIG. 4 (400).

Figure 3A:
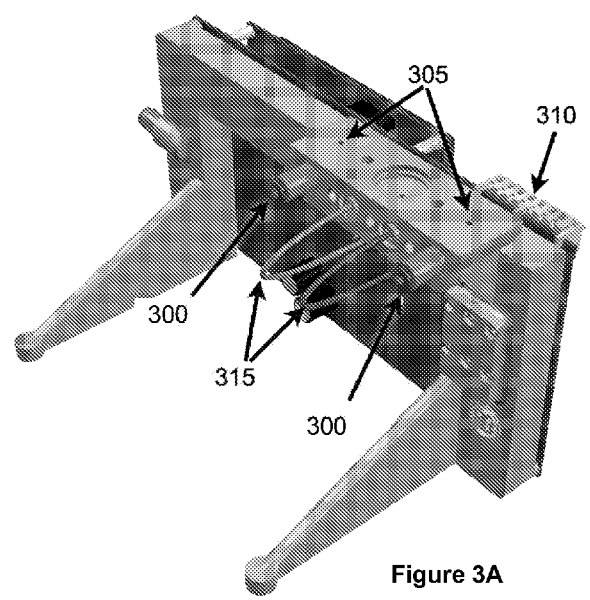
FIG. 3A illustrates a rear perspective view of the modular environmental chamber controller.
Figure 3B:
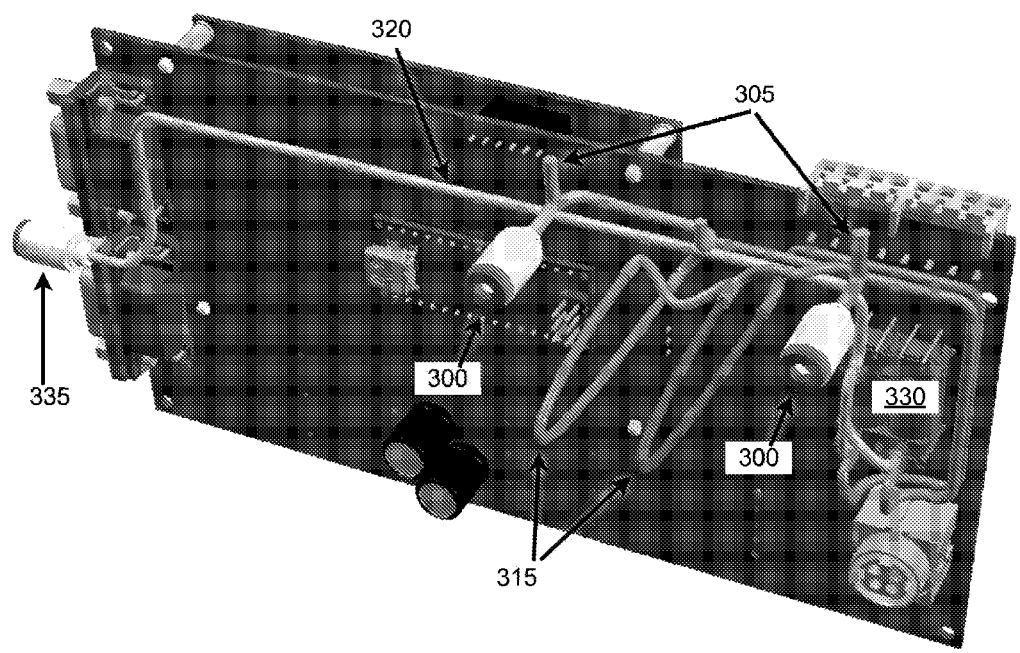
FIG. 3B illustrates a rear perspective view of the modular environmental chamber controller, wherein the manifold body has been made transparent to reveal the internal pneumatic circuits.

With reference to FIGS. 3A and 3B, for example, ⅛"-PTC fittings (300) on the rear of the ECC module may be connected to backplane pneumatic bus (305). Female connectors (310) are used on the electrical output side of the backplane electrical. By accommodating lengths of 1/16"-OD rigid-wall capillary tubing (315), the performance of the modules can individually calibrated by selecting the inner diameter of the capillary tubing and trimming its length. The pneumatic circuits (320) inside the ECC manifold body connect the pneumatic bus (305), pneumatic supply fittings (300), capillary tubing (315), chamber output (335), and solenoid valves (330).

Figure 4A:
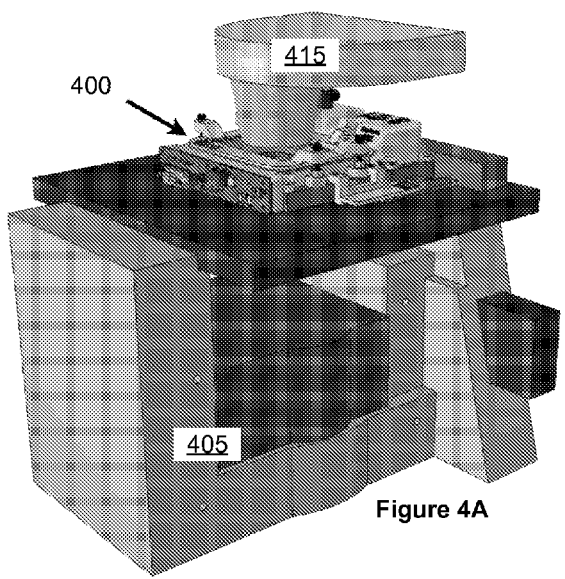
FIG. 4A illustrates a perspective view of an environmental chamber mounted to an inverted microscope stage equipped with a long-working distance condenser.
Figure 4B:
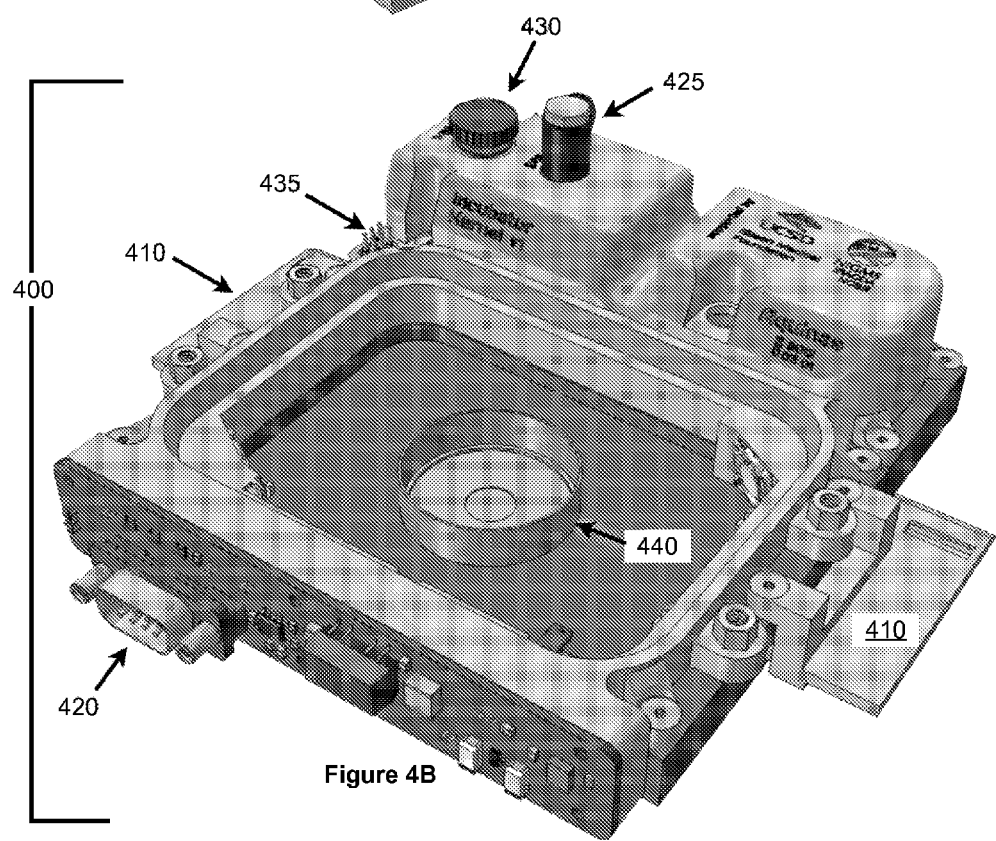
FIG. 4B illustrates a perspective close-up view of an environmental chamber, wherein the lid to the environmental chamber is not present and a 35 mm culture dish is inside the chamber.

With reference to FIGS. 4A and 4B, an environmental chamber (400) can be mounted to a microscope (405) by the use of mounting adapters (410). A long-working distance transmitted light condenser (415) has sufficient clearance for the environmental chamber (400). The cable from the ECC controller is plugged into connector (420). For example, a ⅛"-PTC elbow (425) may supply culture gas and screw plug (430) may be removed to replenish gas-conditioning water. Spring-loaded connector (435) may provide power and data to peripheral modules (e.g. as RFID/NFC hardware, thermoelectric heaters, or active microelectronics in the elastomeric matrix) located on the chamber lid. The environmental chamber may be suitable for cell culture, accommodating standard culture dishes (440).

Figure 5:
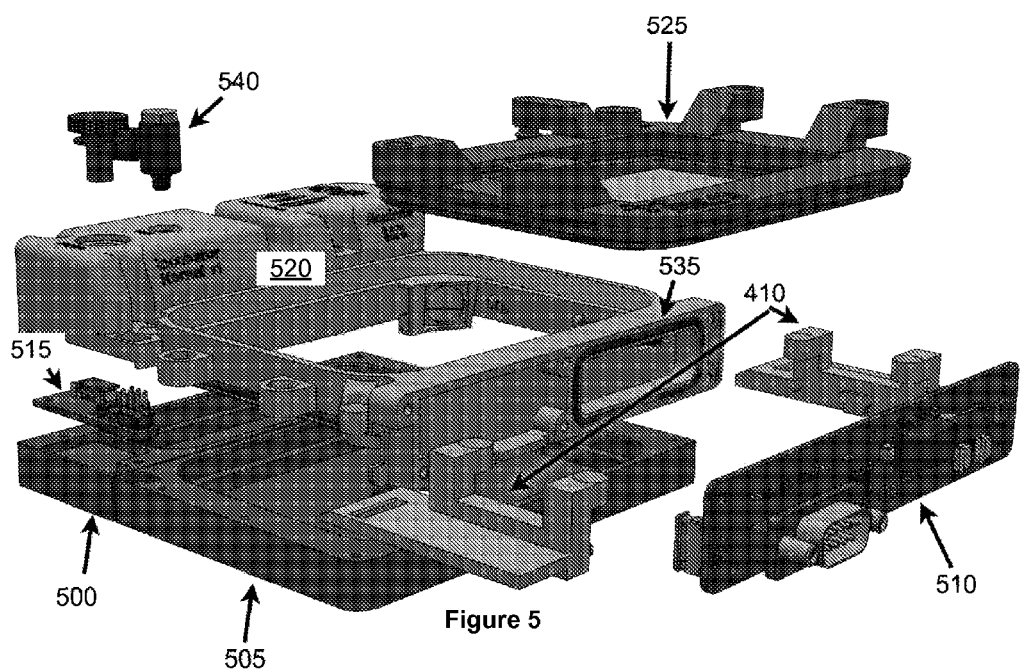
FIG. 5 illustrates a perspective exploded view of the environmental chamber components.

With reference to FIG. 5, the environmental chamber may be comprised of: two machined blocks of aluminum forming the gas conditioning basin (500) and main chamber basin (505); main chamber PCA (510); sensor peripheral PCA (515); a chamber manifold body (520) containing pneumatic circuits; a lid (525); mounting adaptors (410); and miscellaneous standard hardware including o-rings (535), tubing fittings (540), and screws.

Figure 6A:
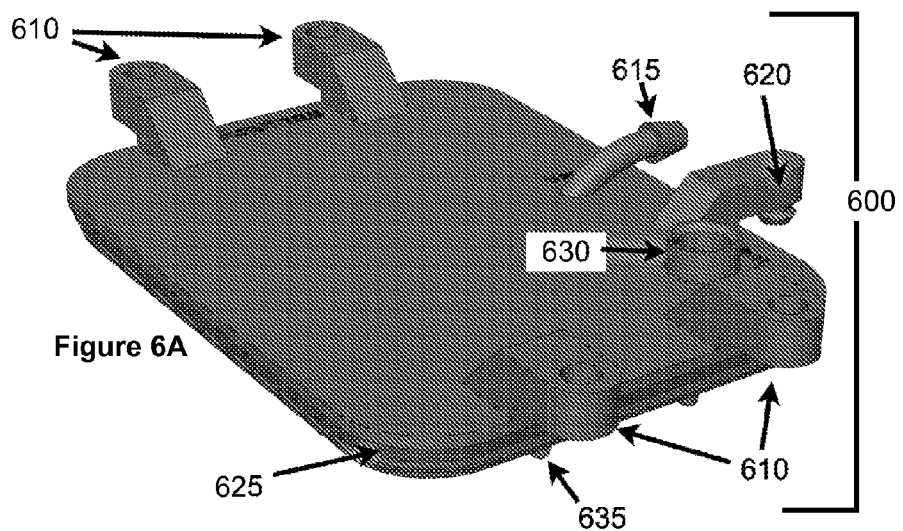
FIG. 6A illustrates a perspective view of a template for the lid of the environmental chamber.
Figure 6B:
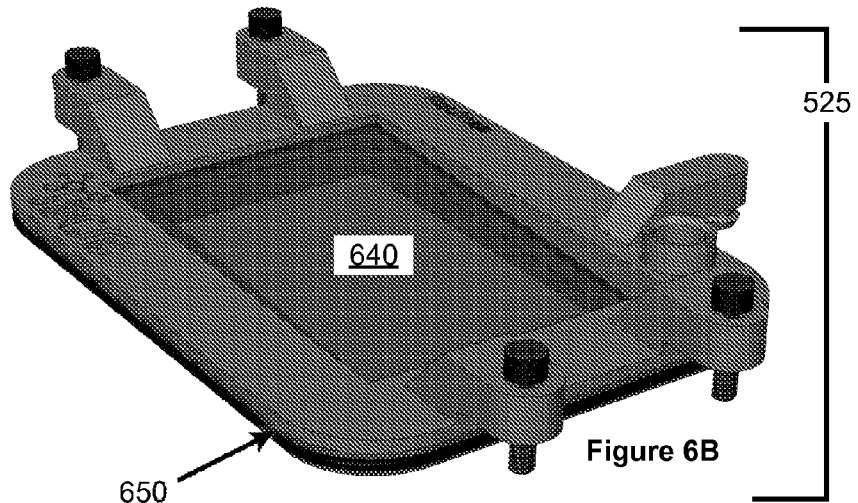
FIG. 6B illustrates a perspective view of a windowed lid for the environmental chamber.
Figure 6C:
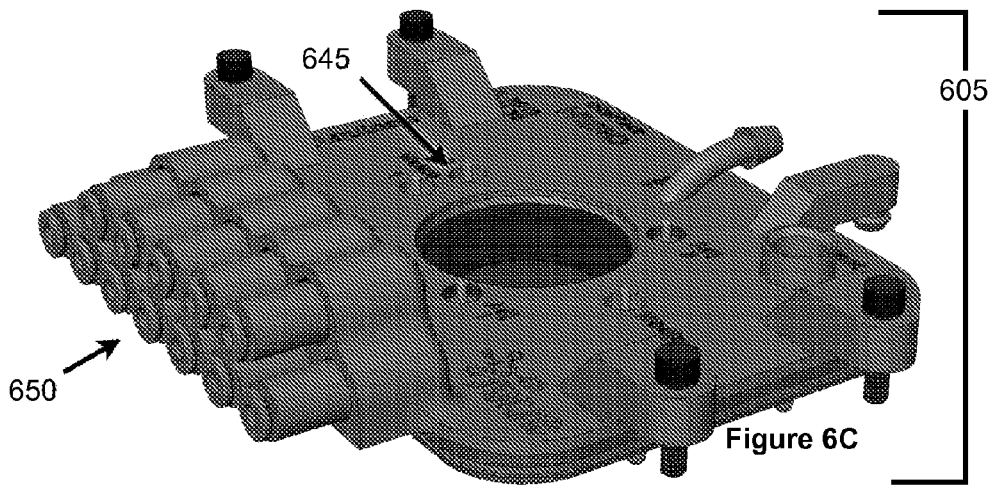
FIG. 6C illustrates a perspective view of a chip-to-world interface lid for the environmental chamber.

With reference to FIGS. 6A, 6B and 6C, the design of the environmental chamber lid may be reconfigurable. A template (600) may serve as a common ancestor from which other versions, including a windowed lid (525) and a chip-to-world interface lid (605), may be derived. The template provides generic features typically common to lid designs, such as: provisions for captive fasteners (610) to secure the lid to the chamber manifold; connection (615) to a vacuum system; connection (620) for conditioned chamber gas; groove (625) to accommodate o-ring (650) in a standard static male glands configuration; chamber gas outlet (630); and, protective bumpers (635). The windowed lid (525) may add a heated window (640) to prevent condensation. The chip-to-world interface lid (605) may add connectors (650) and reservoir-access ports (645).

Figures 7A, 7B:
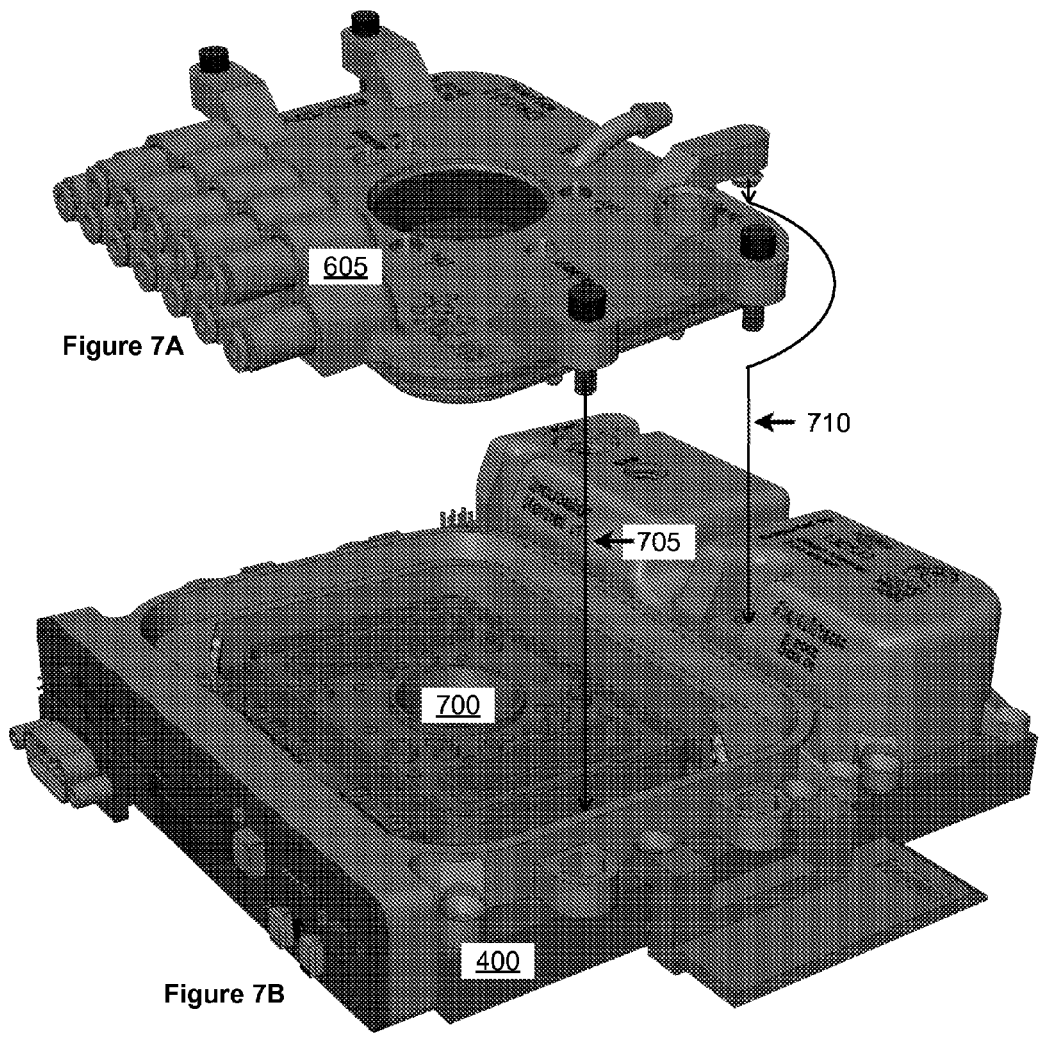
FIG. 7A illustrates a perspective view of a chip-to-world interface lid.
FIG. 7B illustrates a perspective view of an elastomeric matrix inside an environmental chamber.

With reference to FIGS. 7A and 7B, the chip-to-world interface lid (605) may facilitate the operation of an elastomeric matrix (700) inside the environmental chamber (400). The template-based design ensures proper alignment (705) of the lid fastening system, and proper alignment (710) of the connector supplying conditioned chamber gas.

Figure 8A:
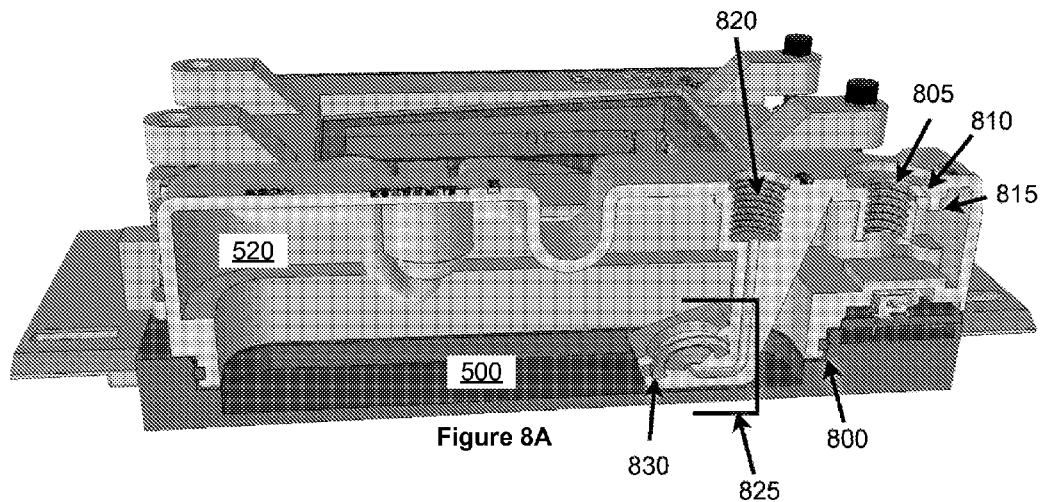
FIG. 8A illustrates a perspective section rear view of gas- and water-handling features which comprise the culture-gas conditioning subsection of the environmental chamber.
Figure 8B:
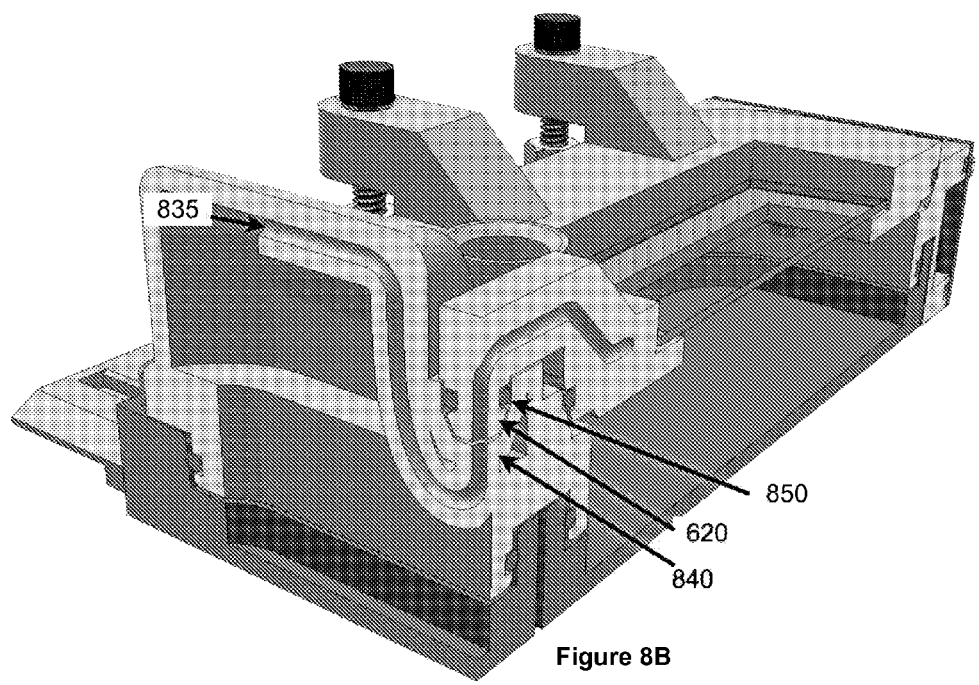
FIG. 8B illustrates a perspective section rear view of pneumatic chamber-to-lid interface features which comprise the culture-gas conditioning subsection of the environmental chamber.

With reference to FIGS. 8A and 8B, the chamber manifold body (520) may be sealed to the gas conditioning basin (500) by an o-ring (800), forming the lumen of the gas conditioning subsystem. Water may be added through port (805). Vent (810) may allow air to escape during filling while the vent extension tube (815) may prevent over-filling. A thin-film flexible heater bonded to the underside of the gas conditioning basin (500) may heat the water inside the gas-conditioning lumen. Dry room-temperature chamber gas may enter at port (820) to gas disperser (825) (which may include accommodations (830) for a fritted disc suitable for gas dispersion). As the chamber gas is dispersed into the heated water, the gas may become humidified and heated. The conditioned chamber gas exits through passageway (835), which may be incorporated into the chamber housing manifold, to port (620), which mates to connector (845), which may be incorporated in the chamber lid, to supply the conditioned gas to the chamber, which may be sealed by o-ring (850) in a standard static male glands configuration.

Figure 9A:
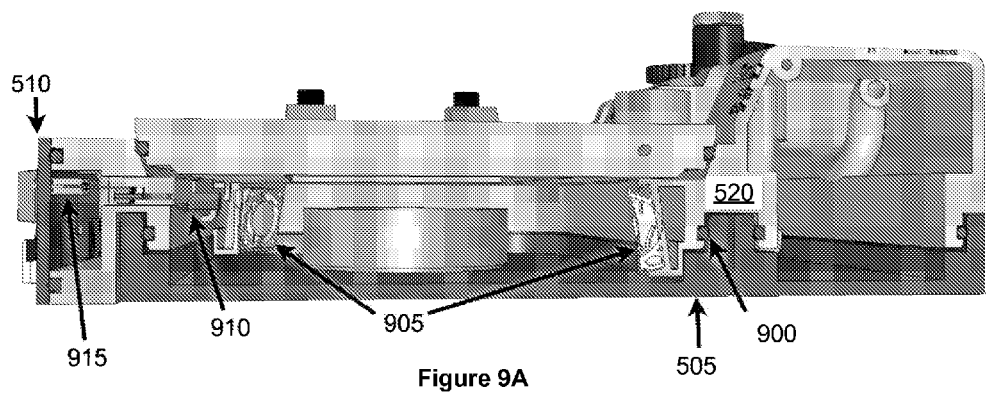
FIG. 9A illustrates a perspective section view of the thermal-management features which comprise the environmental chamber.
Figure 9B:
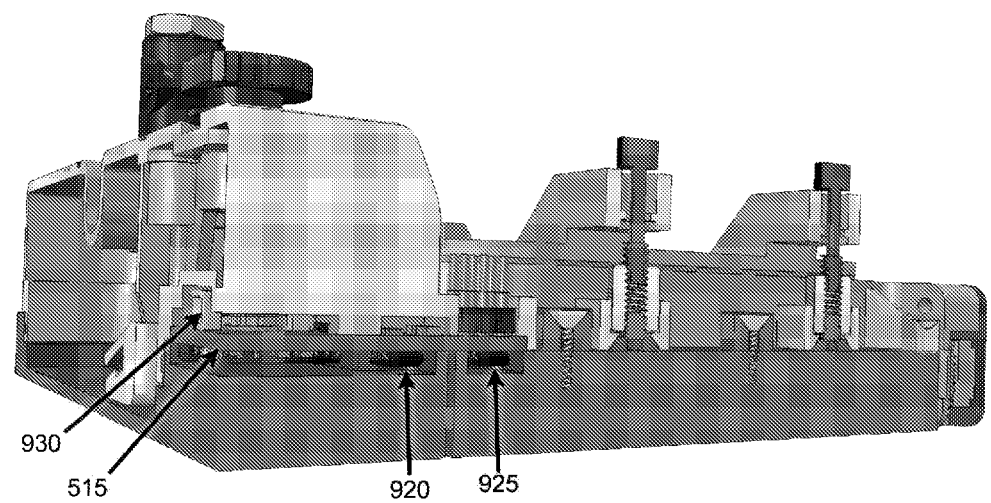
FIG. 9B illustrates a perspective section view of the peripheral sensor printed circuit assembly mounted inside the environmental chamber.

With reference to FIGS. 9A and 9B, the chamber manifold body (520) may be sealed to the chamber basin (505) by an o-ring (900) in a standard static male glands configuration. The chamber atmosphere may be homogenized by stirrer fans (905). A digital sensor (910) measuring both atmospheric temperature and relative humidity may be connected to the ECC module via a digital communication network. A socket (915) facilitates replacement of the digital sensor. The sensor peripheral PCA (515) may include: digital sensor (920) measuring the temperature of the gas conditioning basin; digital sensor (925) measuring the temperature of the main chamber basin, and a connector (930) to main chamber PCA (510).

Two thin-film flexible heaters may be bonded to the underside of the main chamber basin (505).

Figure 10A:
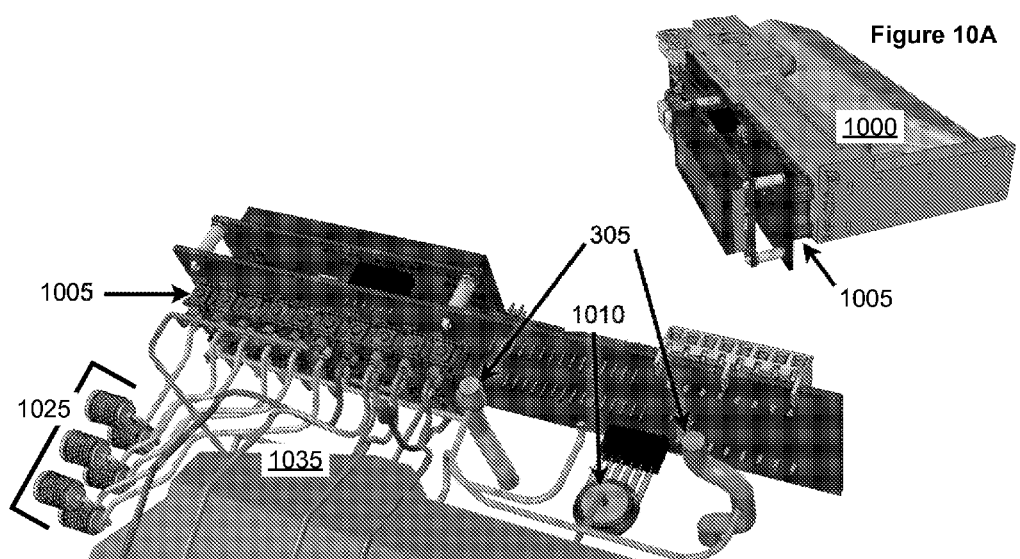
FIG. 10A illustrates a perspective view of a pneumatic output module with eight output ports.
Figure 10B:
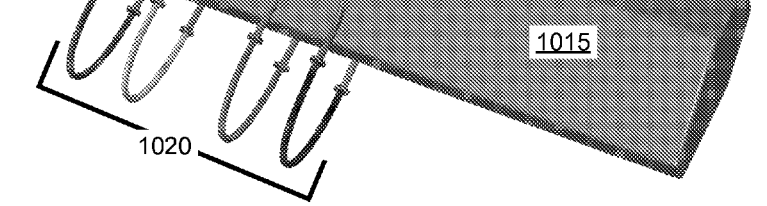
FIG. 10B illustrates a perspective section view of the pneumatic circuits which comprise the manifold body of the pneumatic output module.
Figure 10C:
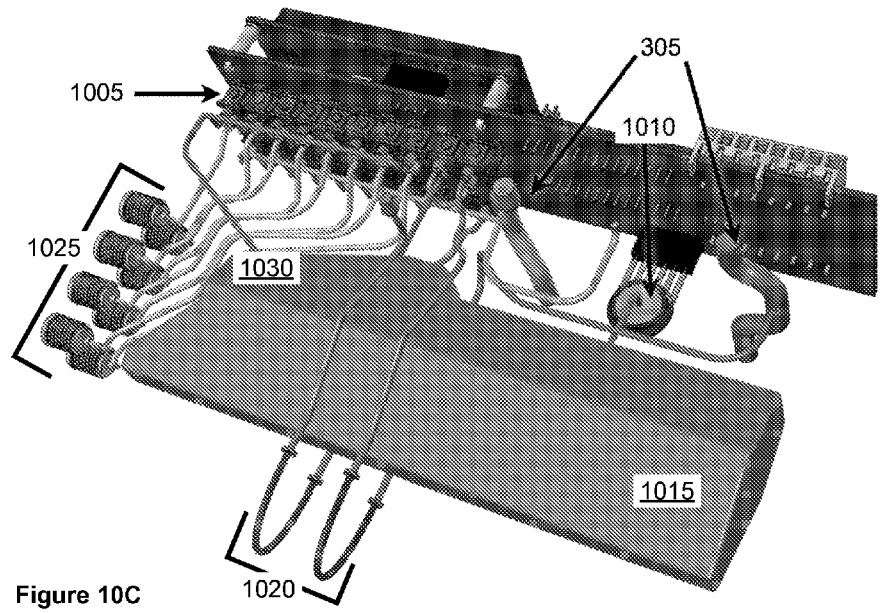
FIG. 10C illustrates a perspective section view of an alternate configuration of the pneumatic circuits which comprise the manifold body of the pneumatic output module.
Figure 11A:
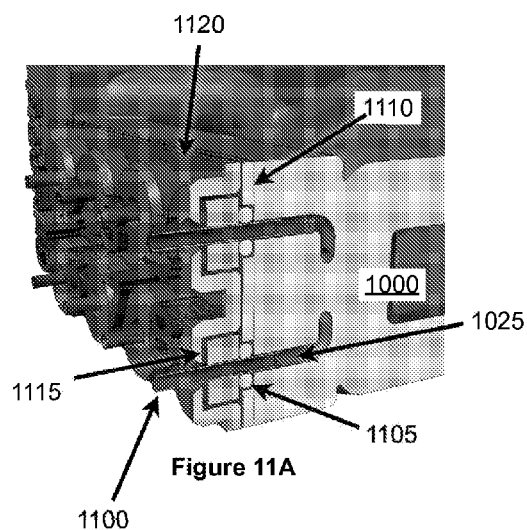
FIG. 11A illustrates a perspective section view of the outputs of the pneumatic output module, configured with magnetic friction-lock ports to facilitate the connection of tubes.
Figure 11B:
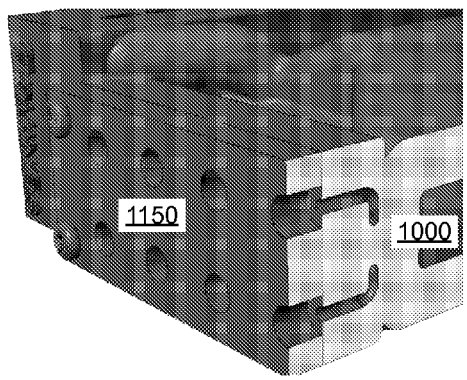
FIG. 11B illustrates a perspective section view of the outputs of the pneumatic output module, configured to accommodate face-sealing threaded connectors.
Figure 11C:
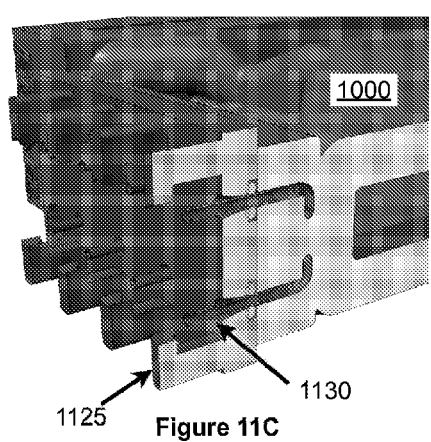
FIG. 11C illustrates a perspective section view of the outputs of the pneumatic output module, configured with crimp-capture features to retain connected tubes.
Figure 11D:
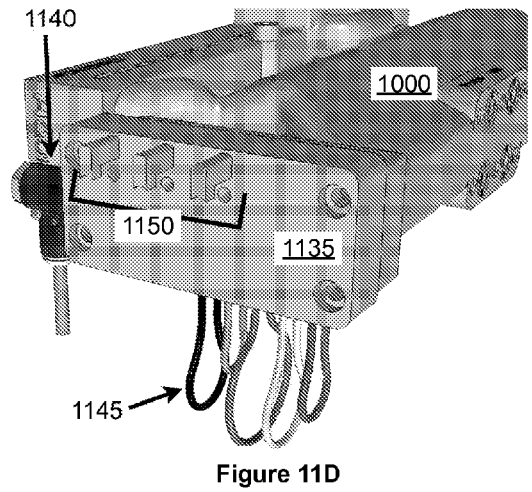
FIG. 11D illustrates a perspective section view of the outputs of the pneumatic output module, configured with a hybrid output module.

With reference to FIGS. 10A, 10B and 10C, the manifold body (1000) of the PO module may incorporate pneumatic circuits connecting: the PCA-mounted solenoid valves (1005) and pressure sensor (1010); the pneumatic backplane (305); an integral pressure accumulator (1015); capillary tubing (1020) and pneumatic output ports (1025). The configuration of the pneumatic circuitry may determine the operation of the PO module. Pneumatic circuitry (1030) may provide eight outputs. Pneumatic circuitry (1035) may provide six outputs, trading-off two outputs in exchange for an improved dynamic response of the pressure regulation. Pressure regulation may be accomplished by varying the duty cycle of an on/off solenoid valve, allowing variable control over the rate of filling and venting of accumulator (1015). A microcontroller may monitor the accumulator using pressure sensor (1010), and accordingly may adjust both the direction (i.e. fill or vent) of accumulator gas flow and the duty cycle (i.e. rate of gas flow in/out of accumulator). Lengths of, for example, 1/16"-OD rigid-wall capillary tubing (1020) may allow fill and vent rates to be individually calibrated by selecting the inner diameter of the capillary tubing and trimming its length.

With reference to FIGS. 11A, 11B, 11C and 11D, the output ports of the PO module may be reconfigurable. Magnetic friction-lock pneumatic ports shown in FIG. 11A may facilitate the connection of tube (1100) which may be sealed by o-ring (1105). A ferromagnetic plate (1110) mounted on the surface of the PO module manifold body (1000) may align o-ring (1105) concentric to output port (1025). The thickness of the ferromagnetic plate (1110) may be sized according to the recommended groove depth of a standard static face-seal glands design appropriate for o-ring (1105). The magnetic attraction between ring magnet (1115) and ferromagnetic plate (1110) may seal o-ring (1105) against both PO module manifold body (1000) and tube (1100). A cover plate (1120) may hold magnet (1115) in place. Tube (1100) may be retained in the connector by friction arising from o-ring (1105). Alternately, crimp-capture features (1125) may be used to retain tube (1130) in place. In a further alternate output configuration, a threaded-plated mounted (1150) to PO module manifold body (1000) may accommodate face-sealing threaded connectors. In a further alternate output configuration, hybrid output module (1135) may be connected to the output ports of the pneumatic control module. Hybrid output module (1135) may: accommodate standard tube fittings (1140), such as 1/8"-PTC elbow illustrated; accommodate capillary tubes (1145); contain reconfigurable output ports (1150); and, pneumatic circuitry. Pneumatic circuitry comprising hybrid output module (1135) modulates the pneumatic outputs of the pneumatic control module. For example, hybrid output module (1135) may incorporate a flow-divider circuit using capillary tube (1145). A hybrid manifold may allow retrofitting and customization of a pneumatic control module.

Figure 12:
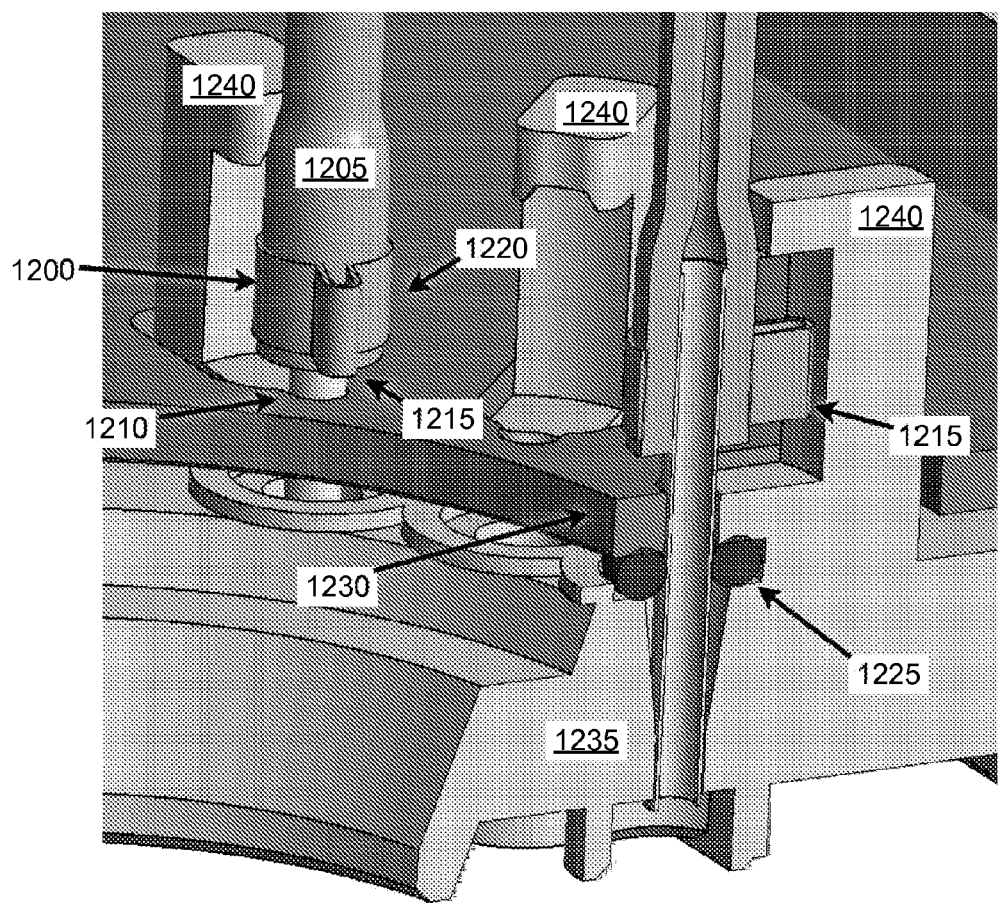
FIG. 12 illustrates a perspective section view of a crimp-capture port.

With reference to FIG. 12, the crimp-capture features (1240) are designed to work with standard 1- and 2-ear crimp bands (1200) (for example OETIKER series 154 "1-Ear Clamps with Insert"). To insert the crimped tubing (1205) into port (1210), the residual crimped ear (1215) may be oriented away (1220) from the retention feature. Once completely inserted, the tube may be rotated to align the residual crimped ear (1215) under the retention feature (1125) to lock the tube in the connector. O-ring (1225) provides the gas tight seal. In this configuration, O-ring (1225), in a standard static female glands configuration, may be captured between a metal cover (1230) and the manifold body (1235) incorporating retention feature (1240).

Figure 13A:
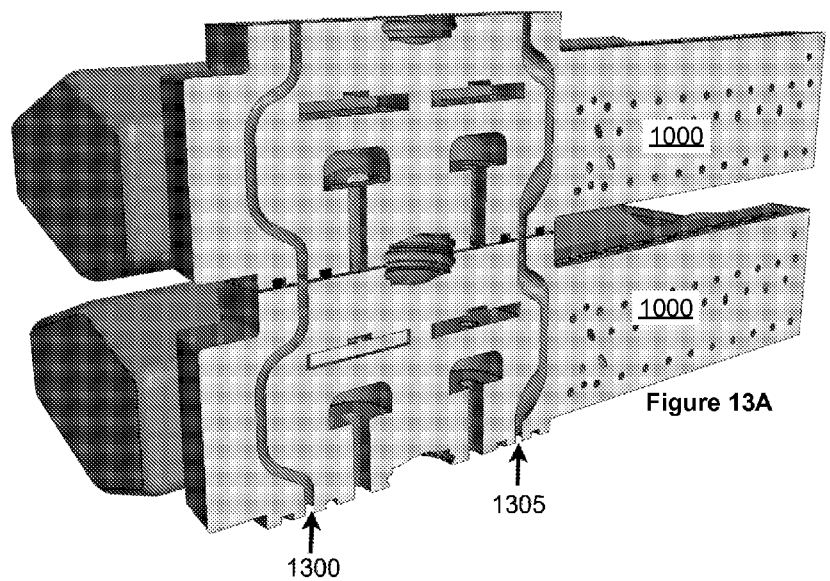
FIG. 13A illustrates a perspective section view of a pneumatic bus which comprises the manifold body of the valve module.
Figure 13B:
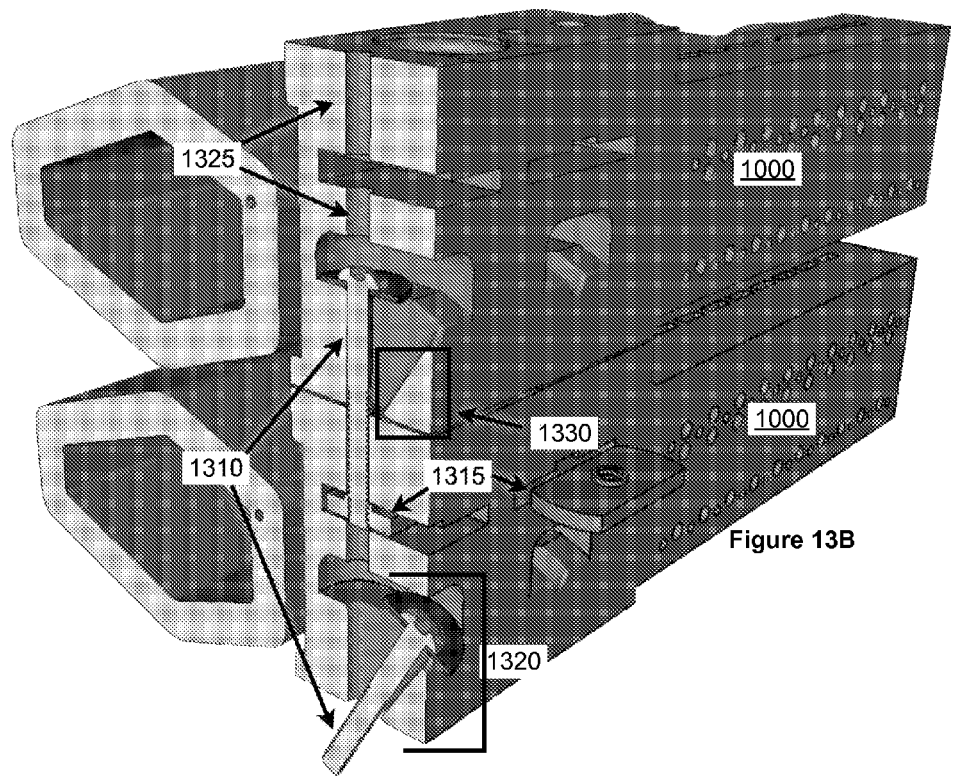
FIG. 13B illustrates a perspective section view of a pneumatic backplane mounting accommodations and features.

With reference to FIGS. 13A and 13B, the control stack may incorporate a two channel pneumatic bus, supplying compressed gas (1300) and a shared exhaust channel (1305). The shared exhaust channel may be used to provide a shared arbitrary pressure reference as an alternative to relying on the ambient atmospheric pressure as the ground reference pressure. Standard screws (1310) and threaded plates (1315) may be used to secure the stacked modules. The PO module manifold body may have accommodations (1320) allowing screw (1310) to be inserted at an angle into the manifold body. After screw (1310) is properly aligned, it may be tightened or loosened by inserting a driver through openings (1325). Alternately, openings (1325) can be made large enough to accommodate vertical insertion of screw (1310). A further alternate accommodation for inserting screw (1310) is removal of portion (1330) of the manifold body (1000).

Figure 14A:
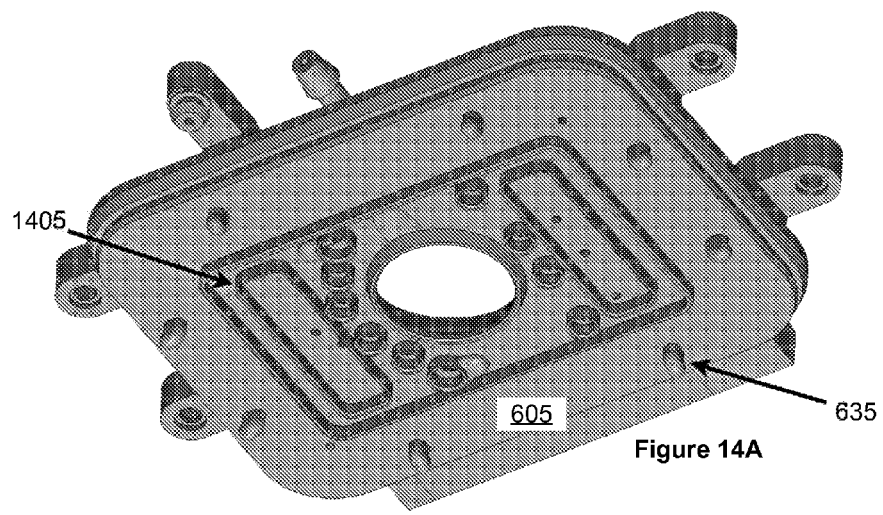
FIG. 14A illustrates a perspective view of a chip-to-world interface.
Figure 14B:
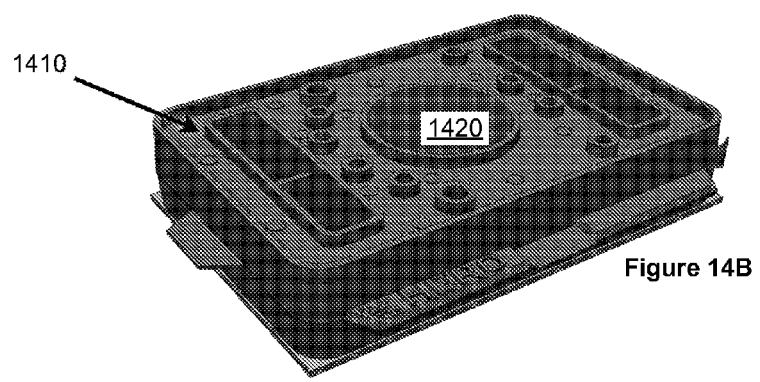
FIG. 14B illustrates a perspective view of an elastomeric matrix which mates to the chip-to-world interface of FIG. 14A.
Figure 14C:
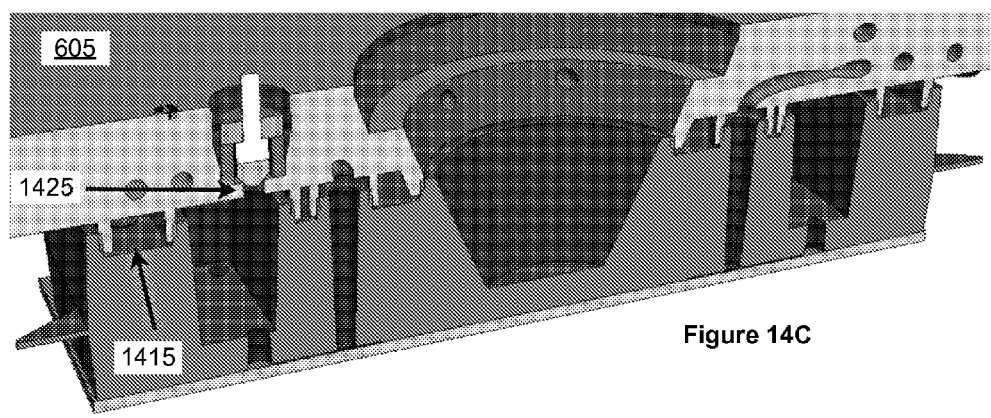
FIG. 14C illustrates a section view of the interlocking features of a chip-to-world interface and an elastomeric matrix.

With reference to FIGS. 14A, 14B and 14C, the chip-to-world interface (605) may include on-interface walls (1405) that interlock with complementary on-chip walls (1410) located on the elastomeric matrix (1420). When interlocked, walled features (1405) and (1410) may form gas-tight seals to create pneumatically-isolated regions. Application of a vacuum to the pneumatically-isolated interstitial space (1415) may not only secure elastomeric matrix (1420) to the chip-to-world interface, but may also improve the sealing performance of the interface features. Reservoir-access ports (1425) on the chip-to-world interface (605) may allow replenishment of the on-chip reservoirs while the elastomeric matrix (1420) is still attached to the chip to world interface. Also, protective bumpers (635) may protect the on-interface walls from damage when the interface is set down on a hard surface.

Figure 15:
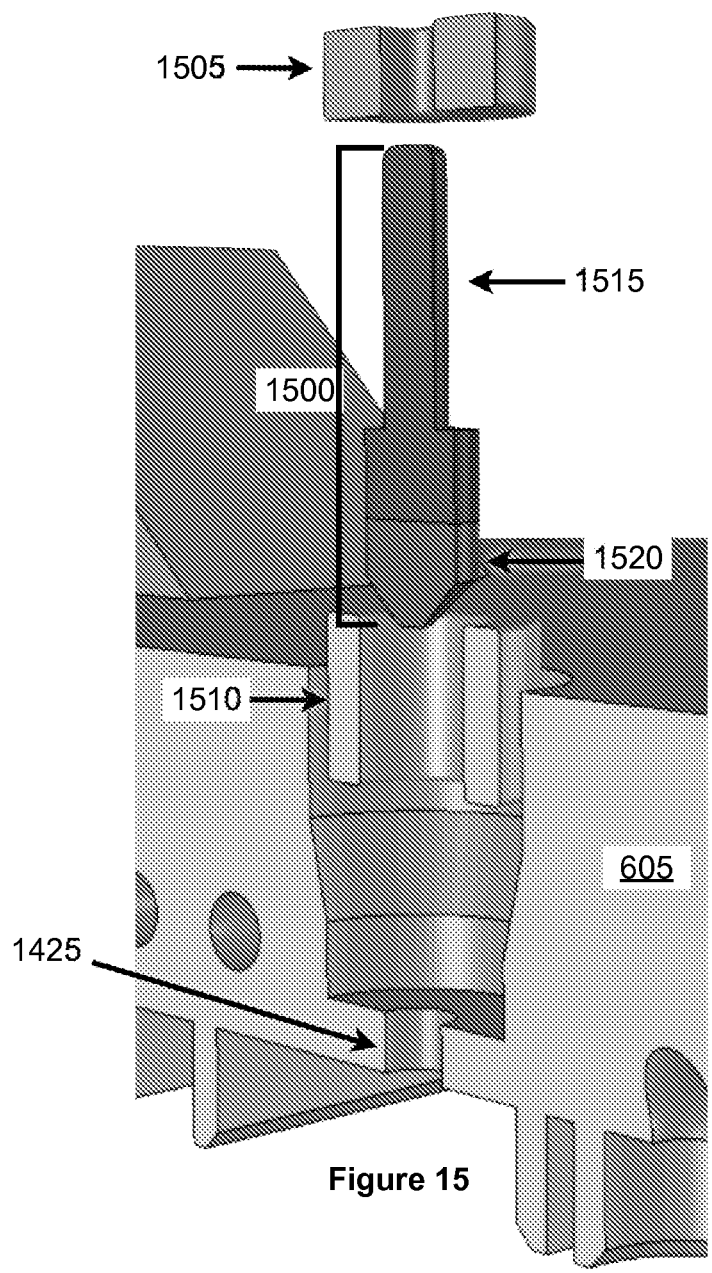
FIG. 15 illustrates a section view of reservoir-access ports comprising the chip-to-world interface manifold body.

With reference to FIG. 15, reservoir-access ports (1425) may be comprised of plug (1500) backed by ring magnet (1505) and ferromagnetic spacer (1510), which may be bonded to the chip-to-world interface (605). The magnetic attraction between spacer (1510) and ring magnet (1505) may lead to a gas-tight seal between plug (1500) against chip-to-world interface (605). Plug (1500) may be a single part fabricated using an additive manufacturing technology capable of building parts from a plurality of materials, such as the Objet Connex350, including a high durometer material (1515) for the stem and a low durometer material (1520) for the sealing surface.

Figure 16:
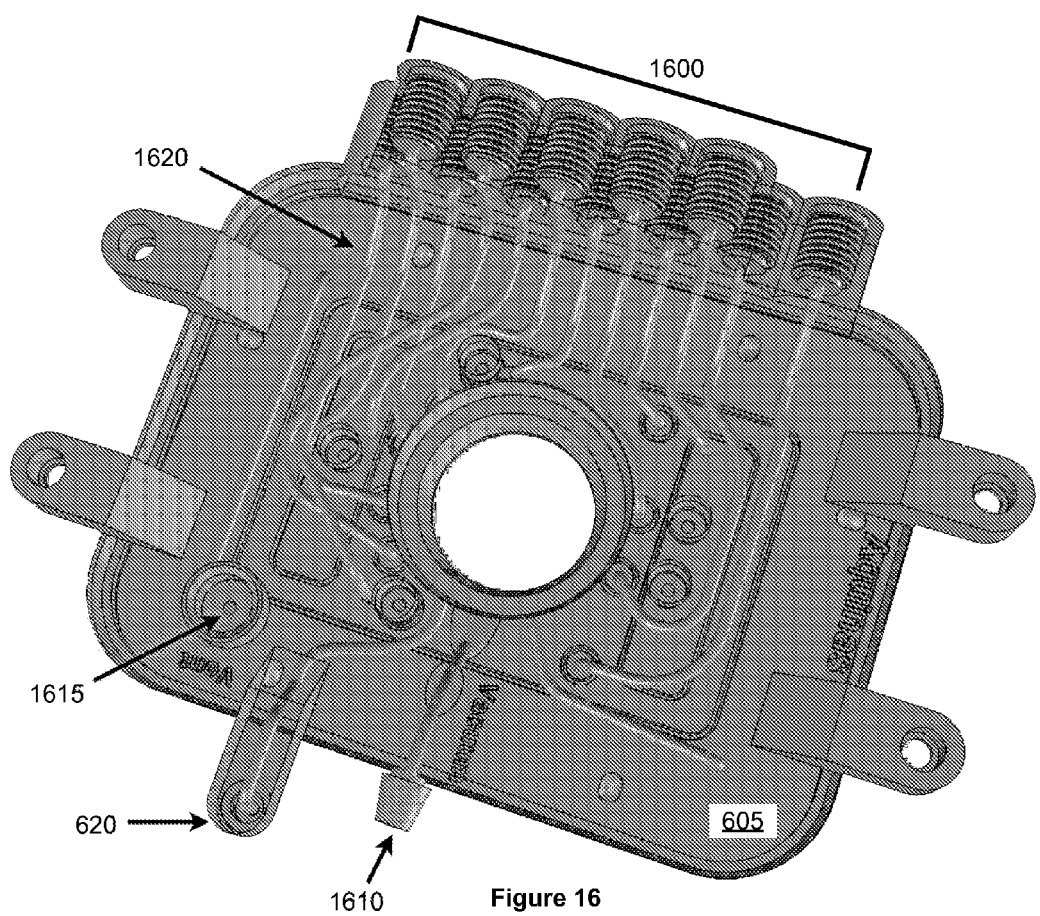
FIG. 16 illustrates a perspective view of pneumatic circuits comprising the manifold body of the chip-to-world interface.
Figure 17A:
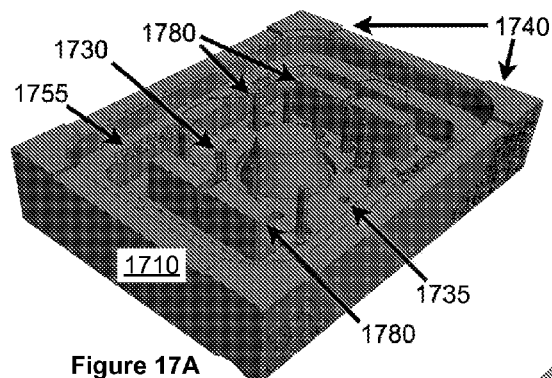
FIG. 17A illustrates a perspective view of upper mold component for the casting of a microfluidic matrix.
Figure 17B:
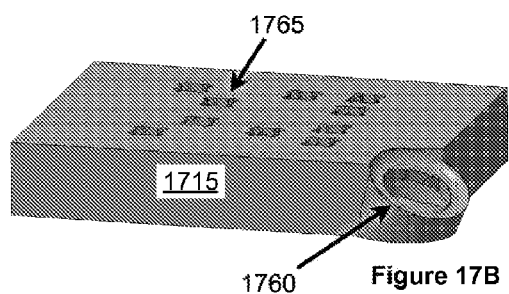
FIG. 17B illustrates a perspective view of ejector-pin cover component for the casting of a microfluidic matrix.
Figure 17C:
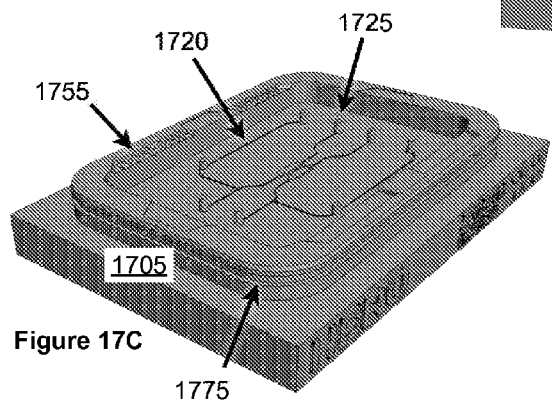
FIG. 17C illustrates a perspective view of lower mold component for the casting of a microfluidic matrix.
Figure 17D:
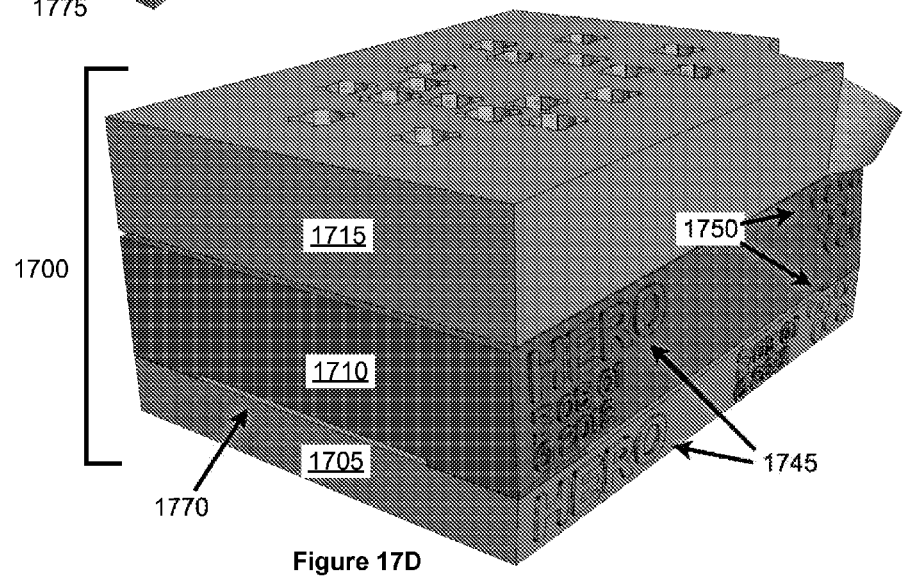
FIG. 17D illustrates a perspective view of assembled double-sided mold for the casting of a microfluidic matrix.
Figure 19D:
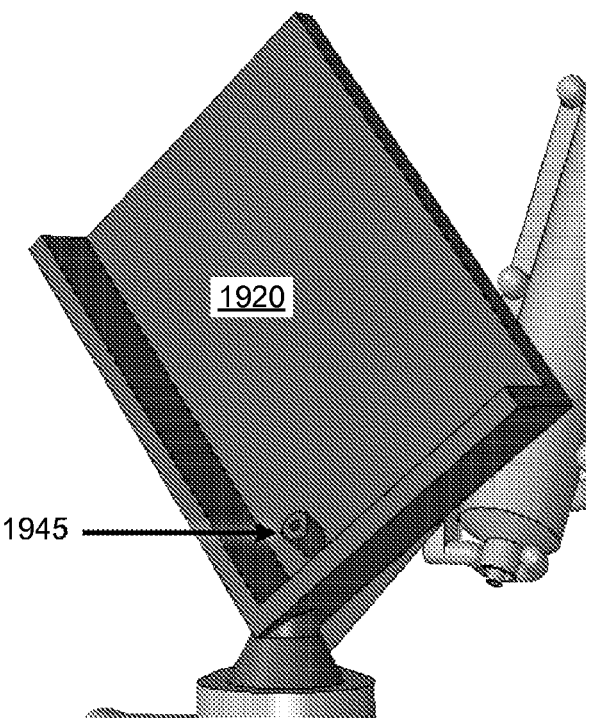
FIG. 19D illustrates a perspective view of orientation and injection features comprising the casting apparatus.
Figure 19E:
FIG. 19E illustrates a perspective view of clamping assembly comprising the casting apparatus.

With reference to FIG. 16, pneumatic circuits (1620) incorporated into the chip-to-world interface (605) connect: the pneumatically-isolated regions formed after mating elastomeric matrix to the corresponding the chip-to-world interface; connectors (1600) supplying pneumatic control from control system; connector (620) supplying conditioned chamber gas; connector (1610) for applying a vacuum to interstitial region between the elastomeric matrix and chip-to-world interface; vent (1615); and, the lumen of environmental chamber.

With reference to FIGS. 17A, 17B, 17C, and 17D, mold assembly (1700) may be comprised of a mold bottom (1705), mold top (1710), ejector-pin cover (1715), and a plurality of ejector pins. Mold bottom includes an o-ring groove (1775) and patterns for channels (1720) and vias (1725). Mold top may include: on-chip reservoirs patterns (1780); valve pressure chamber patterns (1730); ejector-pin holes (1735); and, mold spacers (1740). Both molds may also incorporate: human-readable marks (1745), machine-readable marks (1750), and tab patterns (1755) for adding marks to the cast elastomeric matrix. Although these molds may be fabricated using additive manufacturing technologies, such as stereolithography or jetted-photopolymer printing, the molds may be produced by any method of adequate resolution, such as wire machining. The ejector pin cover includes vent fitting receptacle (1760) and ejector-pin holes (1765). Mold spacer features (1740) maintain parting gap (1770) on mold assembly (1700). Parting gap may be measured to serve as an indicator of proper mold alignment and setup. Furthermore, parting gap facilitates the separation of the mold top and bottom by allowing flat-bladed tool, such as a flat screwdriver or metal spatula, to slide between and pry apart the mold halves.

With reference to FIGS. 18A, 18B and 18C, unpolymerized polymer may enter mold assembly (1700) through injection port (1800) on bottom mold (1705). Vent (1805) on top mold (1710) may be closed after the mold is filled with polymer. Ejector-pin hole (1735) may be sealed by ejector-pins during mold assembly. After polymerization, the ejector-pins may facilitate removal of the elastomeric matrix from the mold.

With reference to FIGS. 19A-19E, casting apparatus (1900) may be comprised of mold assembly (1700), vent fitting (1905), syringe adaptor (1910), mold stand (1920), base (1925), syringe holder (1930), syringe (1935), and mold clamp (1940). The procedure for using casting apparatus (1900) may be as follows: mold assembly (1700) is clamped to mold stand (1920) using mold clamp (1940); syringe (1935), containing unpolymerized elastomer, is place in syringe holder (1930), and a tube is connected between syringe and injector inlet (2020); a syringe adaptor is used to pressurize syringe (1910), filling mold assembly (1700); a valve attached to vent fitting (1905) is closed after mold assembly is filled with polymer; and, the polymer is allowed to cure in mold assembly (1700) under pressure. Vent fitting (1905) has flange (1950), which allows vent fitting (1905) to be inserted into vent fitting receptacle (1760), and subsequently locked in place by rotating vent fitting (1905). Syringe adaptor (1910) may have a groove (1915) for an o-ring in a standard static male glands configuration. Mold stand (1920) may include an injector (1945) which mates with bottom mold.

Figure 20:
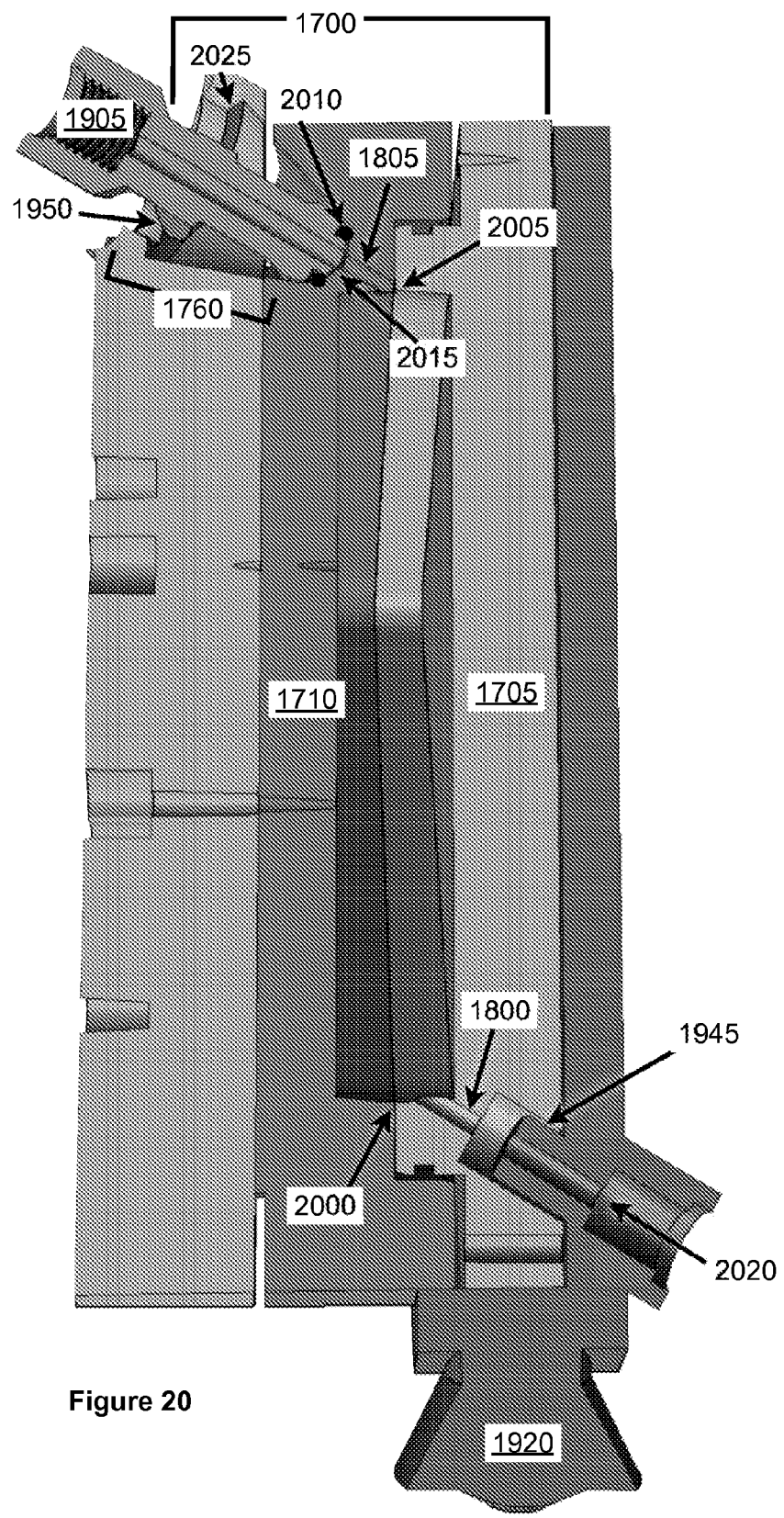
FIG. 20 illustrates a perspective section view of mold oriented on casting apparatus.

With reference to FIG. 20, mold stand (1920) orients mold assembly (1700) to create low-point (2000) and high-point (2005), corresponding respectively to injection port (1800) and vent (1805). This may help eliminate bubbles from the molds and lower defect rates in the finished devices. O-ring (2010), configured similar to a standard static male glands configuration, seals vent fitting (1905) against at mating surface (2015) located on top mold (1710). Unpolymerized polymer may enter through injector inlet (2020). Vent fitting receptacle (1760) may allow the vent fitting (1905) to be inserted and locked in place by rotating vent fitting (1905) to align vent fitting flanges (1950) with vent receptacle flanges (2025). If mating surface (2015) is hemispherical, the operation of vent fitting (1905) may be tolerant of misalignment and minor movement during insertion and operation, improving reliability of the casting process. An o-ring, in a standard static tube-fitting boss configuration, between injector (1945) and bottom mold (1705) prevent leakage of polymer when filling mold.

Figure 21A:
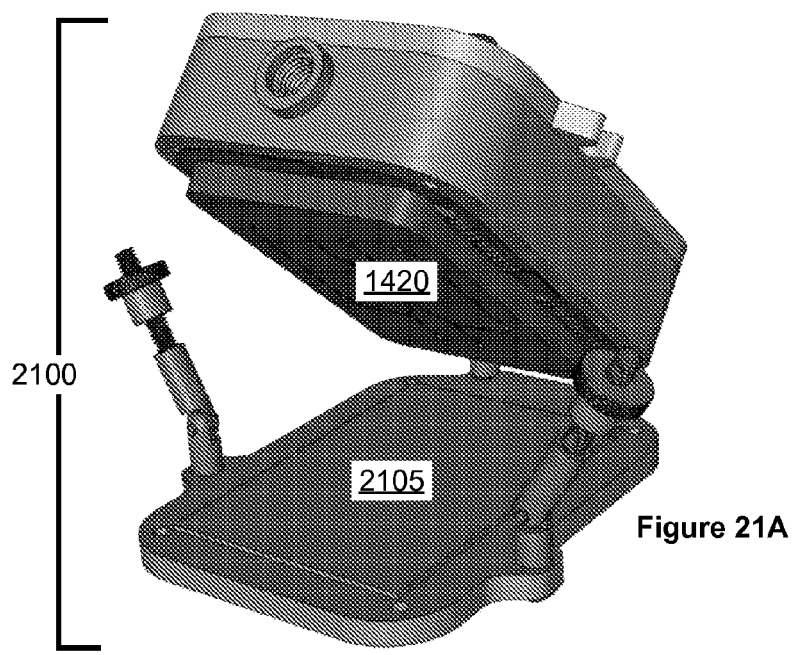
FIG. 21A illustrates a perspective view of a substrate pressure bonder, loaded with a microfluidic device and substrate, in an open position.
Figure 21B:
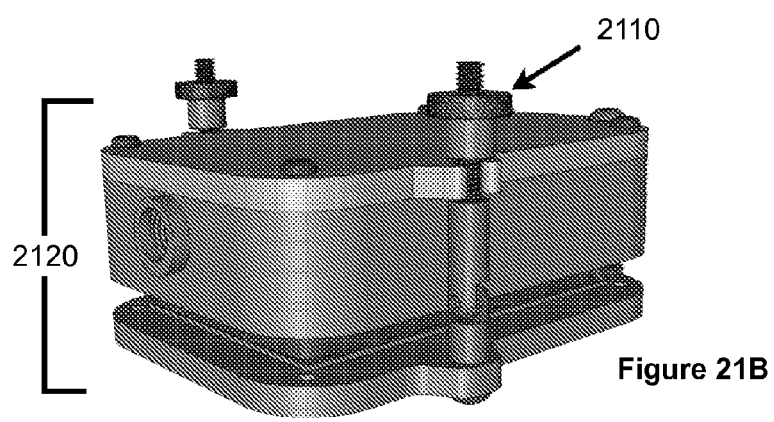
FIG. 21B illustrates a perspective view of a substrate pressure bonder, loaded with a microfluidic device and substrate, in a closed position.
Figure 21C:
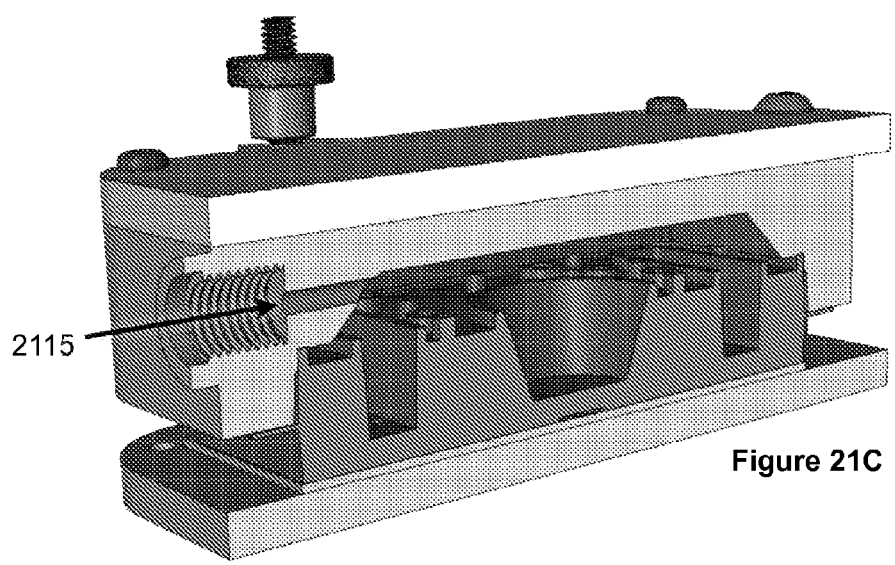
FIG. 21C illustrates a perspective section view of a substrate pressure bonder, loaded with a microfluidic device and substrate, in a closed position.

With reference to FIGS. 21A, 21B and 21C, pressure bonder (2100) facilitates the bonding of elastomeric matrix (1420) to substrate (2105). After loading with elastomeric matrix and substrate, pressure bonder may be closed (2120) to bring elastomeric matrix in contact with substrate. Subsequently, clamps (2110) may be engaged and pressurized gas is introduced through port (2115).

Figure 22A:
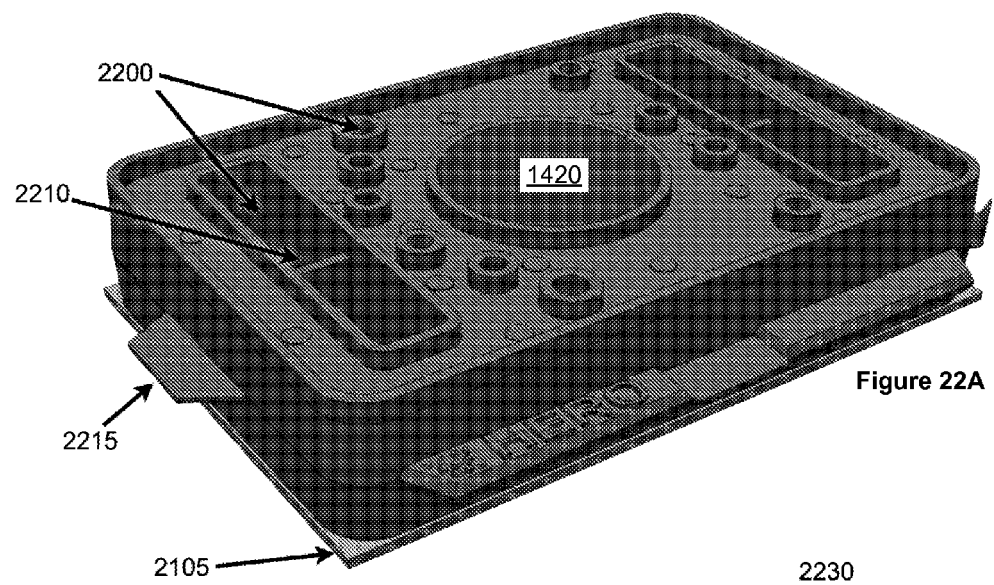
FIG. 22A illustrates a perspective view of a microfluidic matrix with on-chip solution reservoirs and its chip-to-world interface features.
Figure 22B:
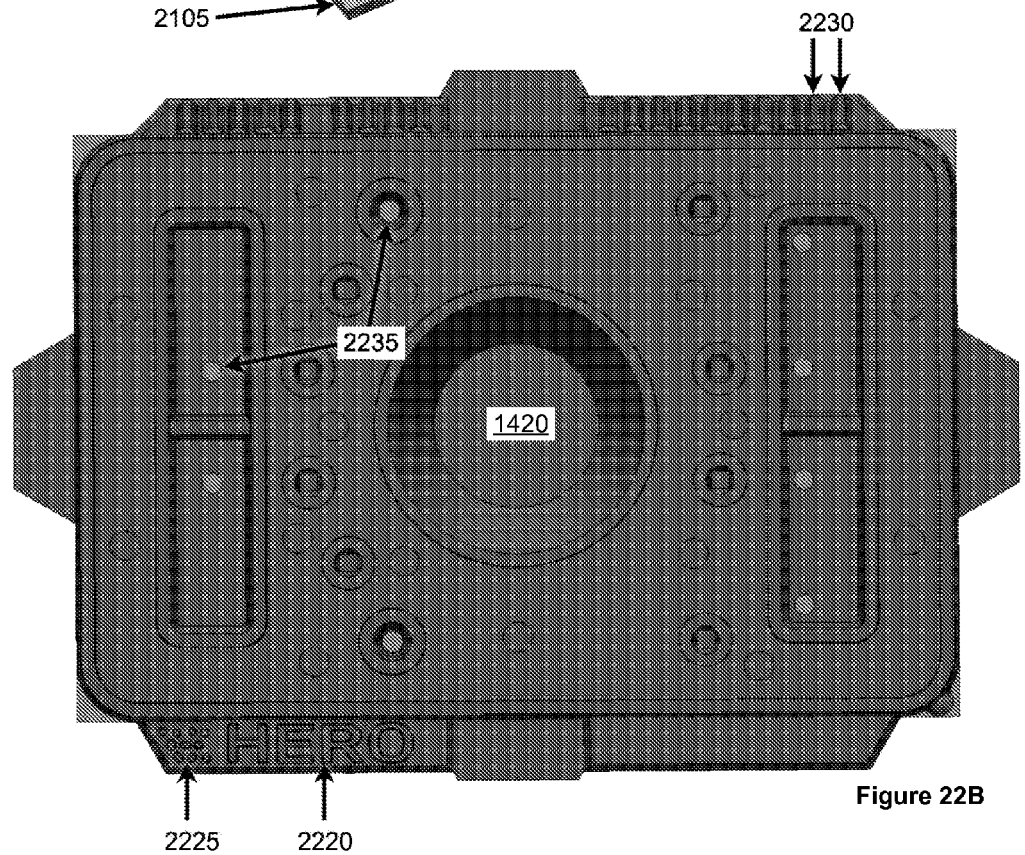
FIG. 22B illustrates an overhead view of a microfluidic matrix with on-chip identifiers and quality control features.

With reference to FIGS. 22A and 22B, the elastomeric matrix (1420) may incorporate features to improve usability and quality control. On-chip reservoirs (2200) facilitate handling of liquids and can be configured in a plurality of shapes and volumes. Reservoir dividers (2210) segregate liquids within a single reservoir. Substrate (2105) is visible through via (2235), which serves as an entry point into channels located on the lower surface of the elastomeric matrix. The thickness of fiducial tabs (2215) on the matrix can be measured and serve as acceptability criteria. Marking tabs on the matrix allow the addition of human-readable marks (2220) and machine-readable marks (2225) marks. Tear-away tabs (2230) allow manual coding of individual elastomeric matrices.

Figure 23A:
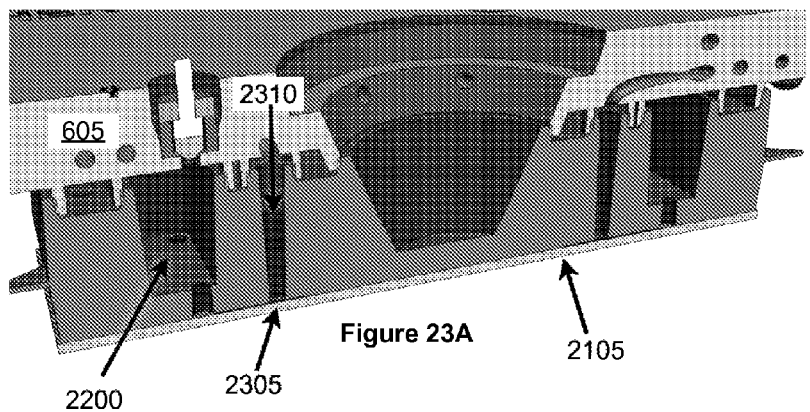
FIG. 23A shows a perspective section view of structure of the microfluidic matrix/chip-to-world interface and reservoir replenishment ports.
Figure 23B:
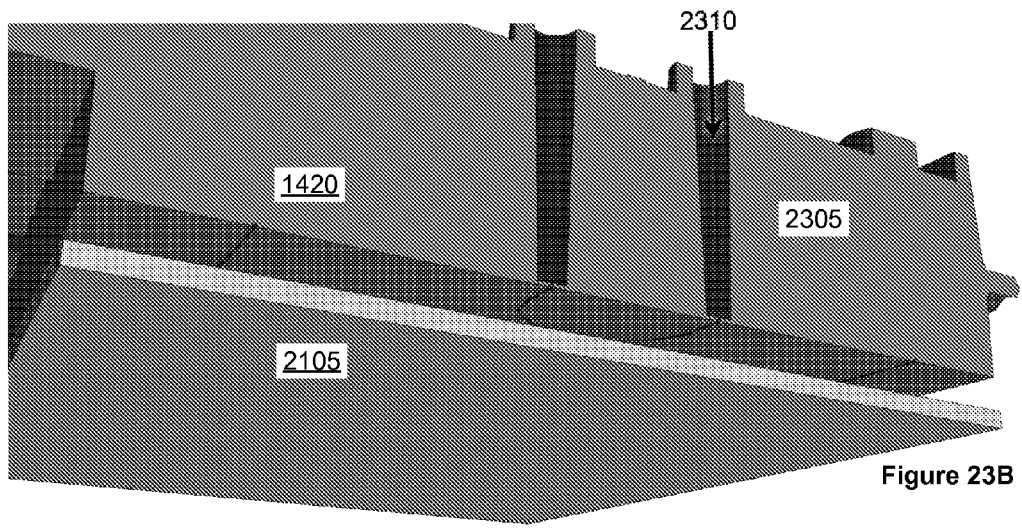
FIG. 23B shows a perspective section view of channel and valve comprised of elastomeric matrix and substrate.
Figure 23C:
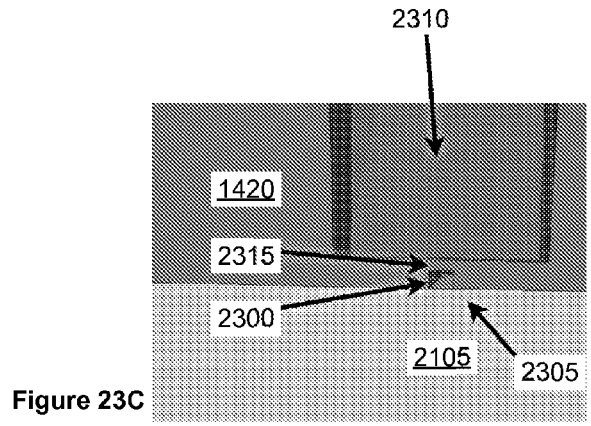
FIG. 23C is a close-up view of the valve of FIG. 23A.

With reference to FIGS. 23A, 23B and 23C, channel (2300) may be created with an elastomeric matrix (1420) and substrate (2105) each forming a portion of the channel. In FIG. 23B, elastomeric matrix (1420) is shown separated from substrate (2105) to illustrate the channel features on the bottom surface of elastomeric matrix (1420). Valve (2305) can be created by adding pressure chamber (2310) directly above channel (2300), such that diaphragm (2315) is disposed between the channel (2300) and pressure chamber (2310). Diaphragm (2315) can deflect to seal the channel (2300) by the application of pressure to chamber (2310) using chip-to-world interface (605). Valve (2305) requires only a single layer of elastomer, which may subsequently be assembled into multi-layer matrices. The pressure necessary to deflect diaphragm (2315) may be related to thickness of diaphragm and the geometry of channel (2300). For example, 50 psi of pressure may be sufficient to close valve (2305) when the diaphragm thickness is 500 microns and the molds are produced on a PolyJet Objet 30 jetted-photopolymer printer, which may produce channels with rounded profiles. Additionally, the application of pressure to on-chip reservoir (2200) using chip-to-world interface (605) may be used to drive liquids through channels.

Figure 24A:
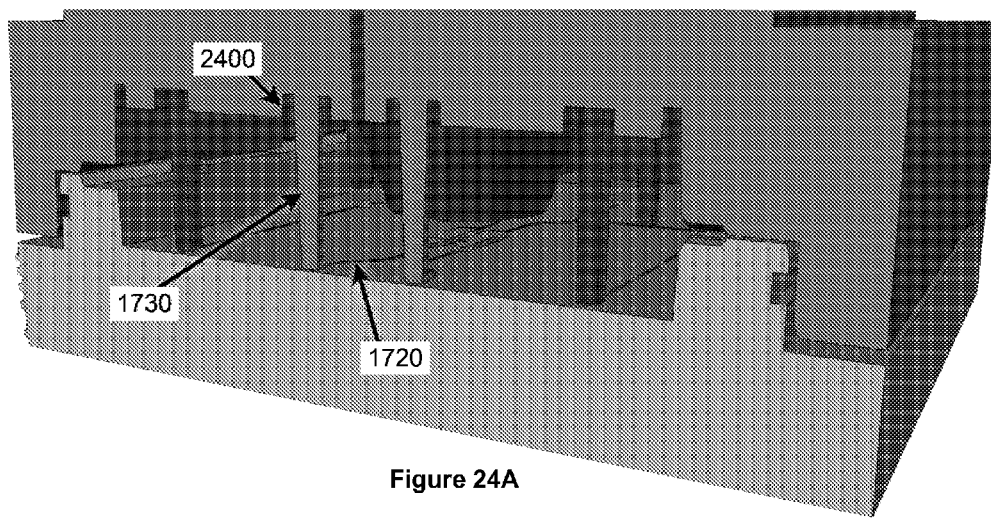
FIG. 24A illustrates a perspective section view of double-sided mold cavity.
Figure 24B:
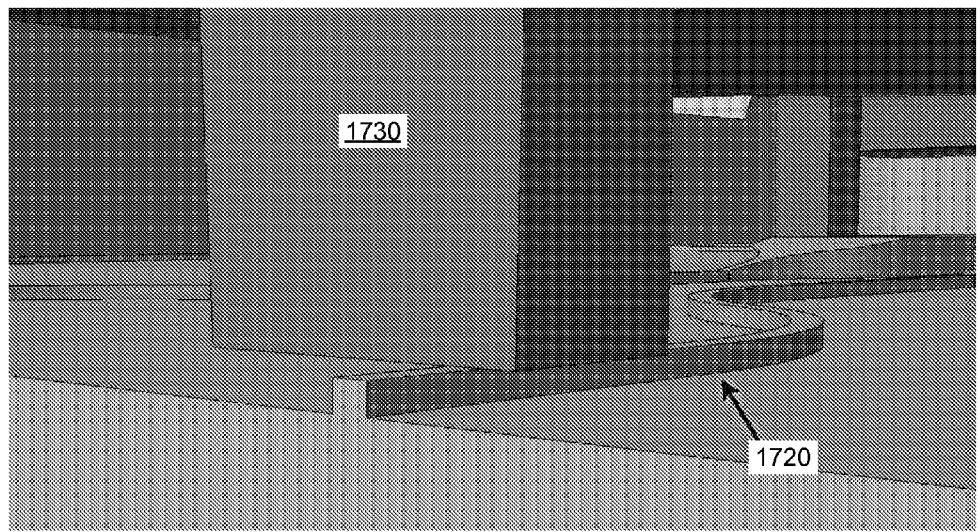
FIG. 24B illustrates a perspective section view of mold configured to cast valve of FIG. 23C.
Figure 26A:
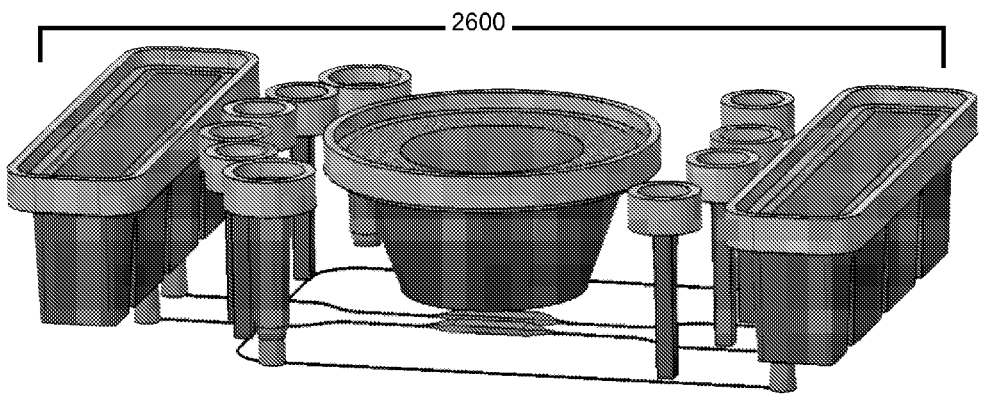
FIG. 26A illustrates a perspective view of microfluidic design master.
Figure 26B:
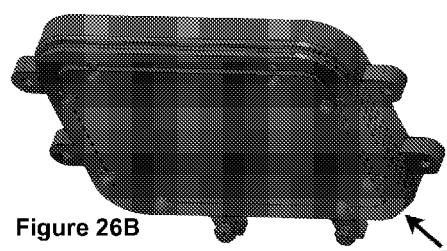
FIG. 26B illustrates a perspective view of template for chip-to-world interface.
Figure 26E:
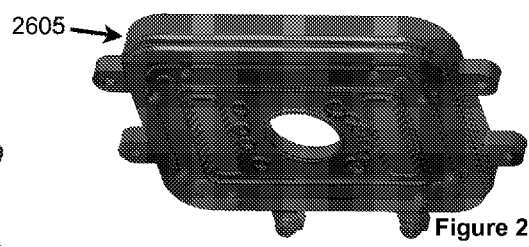
FIG. 26E illustrates a perspective view of derivatized chip-to-world interface
Figure 26C:
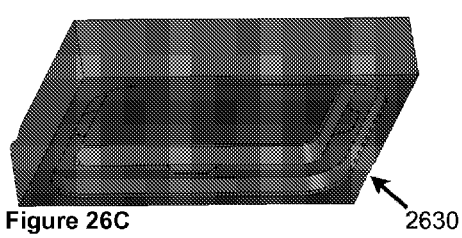
FIG. 26C illustrates a perspective view of template for top mold.
Figure 26F:
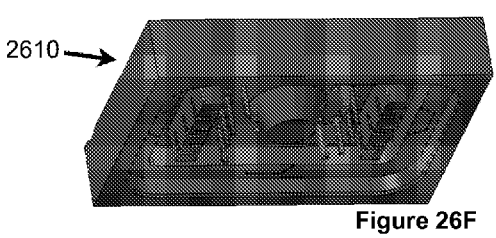
FIG. 26F illustrates a perspective view of derivatized top mold.
Figure 26D:
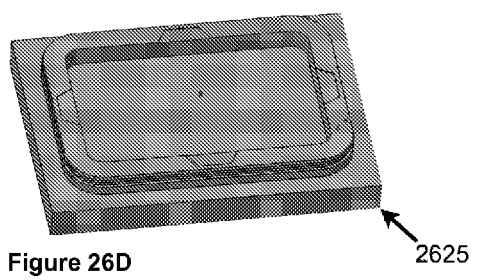
FIG. 26D illustrates a perspective view of template for bottom mold.
Figure 26G:
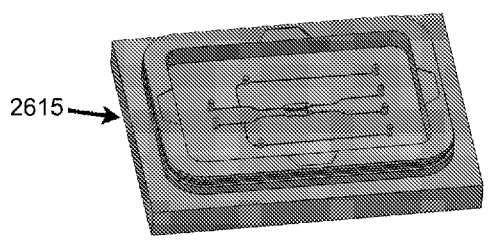
FIG. 26G illustrates a perspective view of derivatized bottom mold.

With reference to FIGS. 24A and 24B, valve (2305) of FIG. 23C may require multiple features: on-chip walls (1410) produced by negative mold pattern (2400); pressure chamber (2310) produced by positive mold pattern (1730); and channel (2300) formed in part by positive mold pattern (1720).

With reference to FIG. 25A-25F, a derived feature may be comprised of a plurality of base features. For example, in order to fabricate and utilize an on-chip reservoir (in an alternate configuration), six base features spanning three real-world entities may be required: crimp-capture (2500), interface passageway (2505), on-interface wall (2510), top mold knockout (2515) (leading to on-chip walls (1410)), top mold buildup (2520) (leading to on-chip reservoir (2200)), and bottom mold buildup (2525) (leading to via 2235). The base features comprising on-chip reservoir can be grouped into a single multi-body object (2530). An internal reference frame may be used to position the comprising base features, which may be represented and stored as distinct solid bodies. A multi-body object may encapsulate all requisite base features and positioning information to fabricate and utilize derived features spanning multiple real-world entities. Use of multi-body object eliminates error-prone manual alignment during the design process, and enables a "cut and paste" approach for designing novel configurations of microfluidic devices.

With reference to FIG. 26A-26G, design master (2600) may encapsulate all base features and positioning information required to fabricate and utilize a given configuration of features. Design master (2600) may be comprised of a plurality of multi-body objects and may also directly include base features. The relative position of the multi-body objects and directly-included base features may rely on a reference frame distinct from the internal reference frames of comprising multi-body objects. For a given design master, final derivatives of the chip-to-world interface (2605), top mold (2610), and bottom mold (2615) may be produced by Boolean combination of the respective templates and relevant solid bodies representing base features. Chip-to-world interface (2605) may be produced by Boolean addition of solid bodies for chip-to-world interface template (2620) and all of the interface buildup features comprising design master. Bottom mold (2615) may be produced by Boolean addition of solid bodies representing bottom mold template (2625) to solid bodies representing bottom mold buildup features comprising design master. Top mold (2610) may be produced first by Boolean subtraction of solid bodies representing top mold knockout features comprising design master from the solid body representing top mold template (2630), followed by Boolean addition of solid bodies representing top mold buildup features comprising design master.

It should be understood, of course, that the foregoing relates to exemplary embodiments of the invention and that modifications may be made without departing from the spirit and scope of the invention as set forth in the following claims.

What is claimed is:

1. An apparatus for operating a pressure-driven microfluidic device, comprising:
   a base module providing a throughput for electrical and pneumatic connections, and the connections including an electrical bus and a pneumatic bus, respectively;
   one or more pneumatic output modules, each pneumatic output module coupled to the electrical bus and the pneumatic bus,
   an environmental chamber having a supply gas input and configured for receiving a microfluidic device;
   wherein each pneumatic output module includes a programmable controller and at least one output channel, the output channel delivering gas according to the programming of the controller to the gas input of the environmental chamber in which the microfluidic device is received, the pneumatic output module further comprising a pneumatic solenoid valve, wherein the output channel delivers gas according to the action of the pneumatic solenoid valve;
   wherein the environmental chamber includes:
      an environmental basin configured for receiving the microfluidic device;
      a gas conditioning basin for conditioning the delivered gas to be provided to the microfluidic device;
      one or more resistive heaters attached to the environmental basin and the gas conditioning basin for temperature control of the microfluidic device and the supplied gas;
      one or more sensors to monitor environmental conditions within the environmental basin, an output of the sensor coupled to the controller; and
      a manifold body with pneumatic circuits for connecting the environmental basin, the gas conditioning basin, and the supplied gas;
   and wherein the electrical bus and the pneumatic bus are common to the base module and the one or more pneumatic output modules.

2. The apparatus of claim 1, including a modular digital environmental chamber controller, comprising: one or more pneumatic outputs supplying chamber atmosphere gas; one or more pneumatic solenoid valves; a reprogrammable microcontroller; external connectors for remote digital environmental sensors capable of powering remote resistive loads; pneumatic and electrical bus connections configured to be shared among several modules; and an additively-manufactured manifold body with internal pneumatic circuits connecting the one or more pneumatic solenoid valves, the one or more pneumatic outputs, and a pneumatic bus.

3. The apparatus of claim 2, wherein the microcontroller is capable of recording diagnostic data indicating an operational condition of the environmental chamber controller.

4. The apparatus of claim 1, wherein the environmental chamber further comprises a lid, and wherein the manifold body is: additively-manufactured and includes internal pneumatic circuits connecting the environmental basin, gas conditioning basin, lid, and supply of gas.

5. The apparatus of claim 4, wherein the environmental chamber is configured to be mounted on an imaging system.

6. The apparatus of claim 4, wherein the electrical bus and the pneumatic bus connect to the lid, and wherein the lid is detachable.

7. The apparatus of claim 6, wherein the lid has a heated transparent window.

8. The apparatus of claim 1, wherein the pneumatic output module further comprises one or more pneumatic output ports, and wherein the manifold body with pneumatic circuits connects the pneumatic solenoid valves, the pneumatic output ports, and the pneumatic bus.

9. The apparatus of claim 8, wherein the controller is configured to record diagnostic data indicating an operational condition of the pneumatic output module.

10. The apparatus of claim 8, wherein the controller of the pneumatic output module is addressable among a plurality of other pneumatic output modules sharing the pneumatic bus and the electrical bus.

11. The apparatus of claim 8, wherein the pneumatic solenoid valves have an integral electronic pneumatic pressure controller delivering a programmable pressure to the pneumatic output ports.

12. The apparatus of claim 8, wherein the pneumatic output ports are modular and accommodate a plurality of configurations.

13. The apparatus of claim 8, wherein a ring magnet seals an O-ring against tubing connected to one of the pneumatic output ports.

14. The apparatus of claim 1, including a monolithic chip-to-world interface for pressure-driven microfluidic devices, comprising: a manifold body with pneumatic connections between the pneumatic circuit and the pressure-driven microfluidic device situated within the environmental chamber, and interlocking features, wherein the features on the manifold body interlock with mating features on a matching microfluidic device.

15. The apparatus of claim 14, wherein a vacuum is used to secure the matching microfluidic device to the chip-to-world interface.

16. The apparatus of claim 14, including resealable ports to access on-chip solution reservoirs without disconnecting the matching microfluidic device from the chip-to-world interface.

17. The apparatus of claim 14, wherein the chip-to-world interface is integrated with the environmental chamber.

18. The apparatus of claim 14, wherein the chip-to-world interface is mounted to an imaging system.

* * * * *